(12) United States Patent
Wong et al.

(10) Patent No.: US 12,318,179 B2
(45) Date of Patent: Jun. 3, 2025

(54) SYSTEMS AND METHODS FOR DETERMINING TIMING FOR FLUORESCENCE BASED BLOOD FLOW ASSESSMENT

(71) Applicant: Stryker Corporation, Portage, MI (US)

(72) Inventors: Vivian Wing Yan Wong, Vancouver (CA); Justin Winston Junyick Choy, Vancouver (CA); Jørgen Walle-Jensen, Vancouver (CA); Hyo Jin Kang, Vancouver (CA)

(73) Assignee: Stryker Corporation, Portage, MI (US)

( * ) Notice: Subject to any disclaimer, the term of this patent is extended or adjusted under 35 U.S.C. 154(b) by 0 days.

(21) Appl. No.: 17/478,864

(22) Filed: Sep. 17, 2021

(65) Prior Publication Data

US 2022/0087548 A1    Mar. 24, 2022

Related U.S. Application Data

(60) Provisional application No. 63/080,637, filed on Sep. 18, 2020.

(51) Int. Cl.
*A61B 1/06*       (2006.01)
*A61B 5/00*       (2006.01)
*A61B 5/0275*    (2006.01)

(52) U.S. Cl.
CPC .......... *A61B 5/0275* (2013.01); *A61B 1/0638* (2013.01); *A61B 5/0071* (2013.01);
(Continued)

(58) Field of Classification Search
CPC ... A61B 5/0275; A61B 1/0638; A61B 5/0071; A61B 5/7405; A61B 5/743;
(Continued)

(56) References Cited

U.S. PATENT DOCUMENTS 8,285,353 B2    10/2012 Choi
10,299,658 B2    5/2019 Yoshizaki
(Continued)

FOREIGN PATENT DOCUMENTS

WO  WO-2017051229 A1 *  3/2017 ........... G06T 11/206
WO  WO-2018104552 A1 *  6/2018 ......... A61B 17/1114
WO     2020/092968 A1    5/2020

OTHER PUBLICATIONS

International Preliminary Report on Patentability dated Mar. 21, 2023, directed to International Application No. PCT/IB2021/058517; 6 pages.

(Continued)

*Primary Examiner* — Joseph M Santos Rodriguez
*Assistant Examiner* — Zainab Mohammed Aldarraji
(74) *Attorney, Agent, or Firm* — Morrison & Foerster LLP

(57) ABSTRACT

A method for performing an assessment related to blood flow in tissue includes receiving fluorescence imaging data associated with movement of a fluorescence imaging agent through a target, determining at least one characteristic associated with a current stage of the movement of the fluorescence imaging agent through the target based on the fluorescence imaging data, comparing the at least one characteristic associated with the current stage to predefined criteria to determine whether the current stage corresponds to a suitable stage for performing an assessment related to blood flow; and, in accordance with the current stage corresponding to the suitable stage, performing the assessment related to blood flow in at least a portion of the target based on the fluorescence imaging data.

24 Claims, 16 Drawing Sheets

(52) U.S. Cl.
CPC ............ *A61B 5/7405* (2013.01); *A61B 5/743* (2013.01); *A61B 5/7475* (2013.01)

(58) Field of Classification Search
CPC ... A61B 5/7475; A61B 5/0261; A61B 5/7264; A61B 5/0064; A61B 5/0086
See application file for complete search history.

(56) References Cited

U.S. PATENT DOCUMENTS

| | | | |
|---|---|---|---|
| 10,783,636 B2 * | 9/2020 | Gurevich | ............ A61B 5/0071 |
| 11,559,607 B2 * | 1/2023 | Kolesky | .............. A61L 27/3804 |
| 2010/0305454 A1 * | 12/2010 | Dvorsky | ............... A61M 5/007 |
| | | | 600/476 |
| 2017/0245766 A1 * | 8/2017 | Flower | ................. A61B 5/0275 |
| 2018/0158187 A1 * | 6/2018 | Gurevich | ............... G16H 50/50 |
| 2018/0160916 A1 * | 6/2018 | Madsen | ............. A61B 17/1114 |
| 2018/0220907 A1 * | 8/2018 | Dvorsky | ................... G06T 7/90 |
| 2022/0087548 A1 * | 3/2022 | Wong | ................. A61B 5/0071 |

OTHER PUBLICATIONS

International Search Report and Written Opinion mailed Jan. 4, 2022, directed to International Application No. PCT/IB2021/058517; 10 pages.

* cited by examiner

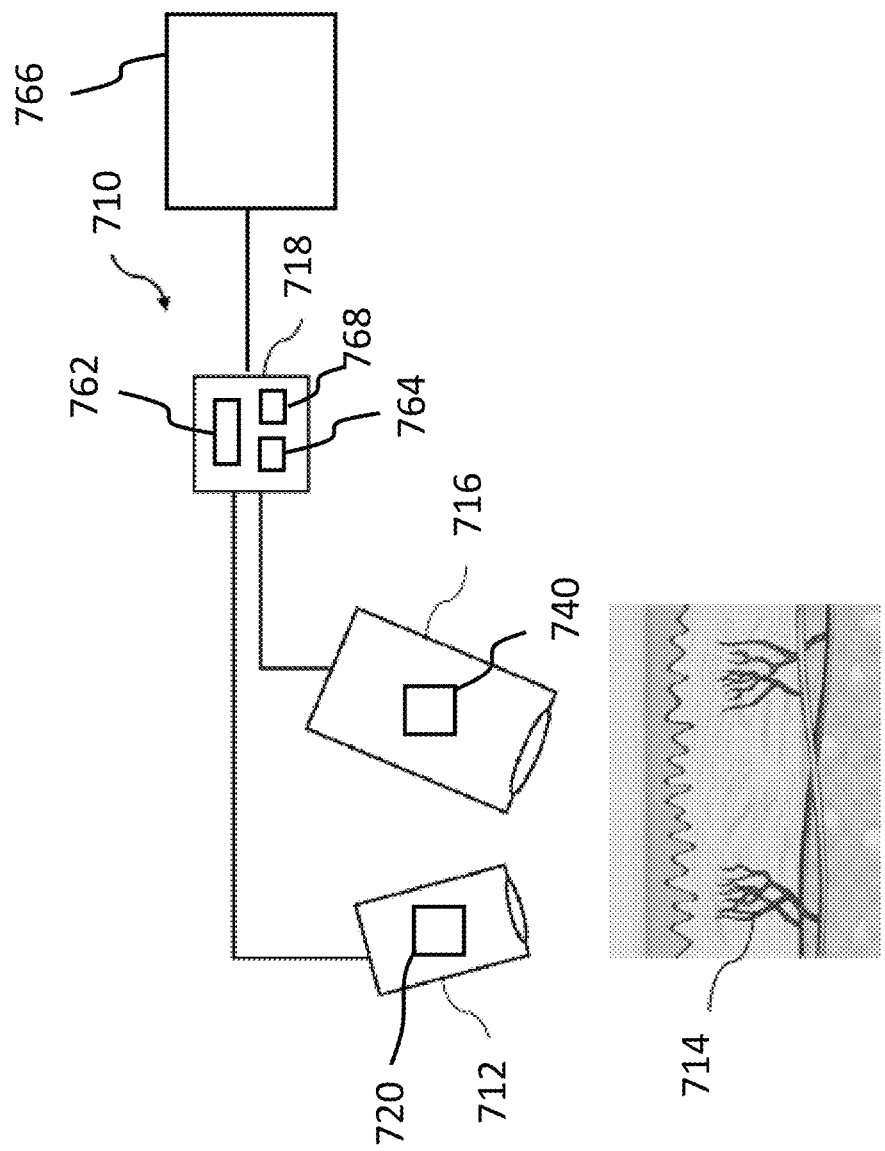

SYSTEMS AND METHODS FOR DETERMINING TIMING FOR FLUORESCENCE BASED BLOOD FLOW ASSESSMENT

CROSS-REFERENCE TO RELATED APPLICATIONS

This application claims the benefit of U.S. Provisional Application No. 63/080,637, filed Sep. 18, 2020, the entire contents of which are hereby incorporated by reference herein.

FIELD

The present disclosure relates generally to medical imaging, and more particularly to fluorescence imaging for analyzing blood flow in tissue of a subject.

BACKGROUND

Medical imaging systems (e.g., endoscopic imaging systems for minimally-invasive surgery or open field medical imaging systems) can help provide clinical information to medical practitioners making decisions (e.g. intraoperative or treatment decisions) based on attributes of tissue of a subject. In many instances, it is useful for medical imaging systems to provide fluorescence imaging for visualizing tissue or attributes of tissue that cannot be visualized or are poorly visualized with white light imaging. Fluorescence imaging generally involves the administration of a bolus of an imaging agent that circulates through the subject's tissue and emits a fluorescence signal when illuminated with the appropriate excitation light. A fluorescence imaging system acquires images of the fluorescence signal emitted by the imaging agent as the bolus passes through the subject's tissue in the imaging field of view. The fluorescence images may be used to make qualitative or quantitative assessments of attributes of the tissue under observation.

Because the amount of imaging agent within the field of view varies over time as the bolus enters and then exits the tissue within the field of view, the timing of a qualitative or quantitative assessment of the tissue under observation may impact the accuracy of the assessment. Conventionally, a medical practitioner may rely on experience to determine the appropriate timing for making qualitative or quantitative assessments when using the fluorescence imaging.

SUMMARY

According to various aspects, systems and methods can determine the timing for performing an assessment related to blood flow in a fluorescence imaging field of view by tracking the progress of the movement of a bolus of fluorescence imaging agent through the imaging field of view and determining when the movement is at a stage suitable for performing the assessment related to blood flow. For example, a determination that a current stage is suitable for performing the assessment related to blood flow may be based on determining that the level of fluorescence intensity within the field of view has stabilized, indicating that the amount of fluorescence imaging agent in the tissue within the field of view is at or near a maximum, which may be the ideal time to perform the assessment. Using the systems and methods described herein according to various aspects, an assessment can be reliably performed at a suitable stage of the movement of the bolus of imaging agent through the target tissue without relying on user observation and experience that can be inaccurate and unreliable.

According to various aspects, a method for performing an assessment related to blood flow in tissue includes receiving fluorescence imaging data associated with movement of a fluorescence imaging agent through a target, determining at least one characteristic associated with a current stage of the movement of the fluorescence imaging agent through the target based on the fluorescence imaging data, comparing the at least one characteristic associated with the current stage to predefined criteria to determine whether the current stage corresponds to a suitable stage for performing an assessment related to blood flow; and, in accordance with the current stage corresponding to the suitable stage, performing the assessment related to blood flow in at least a portion of the target based on the fluorescence imaging data.

Optionally, the suitable stage can be associated with a transition from a net increase in fluorescence imaging agent to a reduced net increase, no net change, or a net decrease in fluorescence imaging agent.

Optionally, the method may further include, prior to performing the assessment related to blood flow, generating at least one indication that the current stage corresponds to the suitable stage.

Optionally, the method may further include generating at least one indication of the current stage.

Optionally, the at least one indication of the current stage may indicate a relative rate that a level of fluorescence imaging agent in the at least a portion of the target is increasing or decreasing.

Optionally, the at least one indication may include a graphical indication of the current stage relative to a nominal progression associated with typical movement of fluorescent imaging agent through tissue.

Optionally, generating the at least one indication may be performed in response to a user input.

Optionally, the at least one indication may include a graphical indication.

Optionally, the graphical indication may indicate a relative leveling over time of an amount of fluorescence imaging agent in the at least a portion of the target.

Optionally, the at least one indication may include an audible indication.

Optionally, the blood flow may be assessed in response to a user input received after the at least one indication is generated.

Optionally, the blood flow may be assessed automatically in response to determining that the current stage corresponds to the suitable stage.

Optionally, performing the assessment related to blood flow may include assessing tissue perfusion of the at least a portion of the target.

Optionally, performing the assessment related to blood flow may include quantifying tissue perfusion.

Optionally, the at least one characteristic may include a rate of change of a level of fluorescence intensity.

Optionally, the level of fluorescence intensity may be an average fluorescence intensity.

Optionally, the at least one characteristic may include a standard deviation of fluorescence intensity.

Optionally, comparing the at least one characteristic to predefined criteria may include comparing a current rate of change of a level of fluorescence intensity to a previous rate of change of the level of fluorescence intensity.

Optionally, the fluorescence imaging data may be received from an imager during a medical procedure.

Optionally, the fluorescence imaging data may include endoscopic imaging data or open-field imaging data.

According to various aspects, a system for guiding assessment related to blood flow includes one or more processors, memory, and one or more programs, wherein the one or more programs are stored in the memory and configured to be executed by the one or more processors, the one or more programs including instructions for: receiving fluorescence imaging data associated with a fluorescence imaging agent moving through a target, determining at least one characteristic associated with a current stage of movement of the fluorescence imaging agent through the target based on the fluorescence imaging data, comparing the at least one characteristic associated with the current stage to predefined criteria to determine whether the current stage corresponds to a suitable stage for performing an assessment related to blood flow, and in accordance with the current stage corresponding to the suitable stage, performing the assessment related to blood flow in at least a portion of the target based on the fluorescence imaging data.

Optionally, the system may further include an imager for generating the fluorescence imaging data associated with a fluorescence imaging agent moving through a target.

Optionally, the system may further include an illuminator for generating excitation light for exciting the fluorescence imaging agent.

Optionally, the suitable stage may be associated with a transition from a net increase in fluorescence imaging agent to a reduced net increase, no net change, or a net decrease in fluorescence imaging agent.

Optionally, the one or more programs may include instructions for, prior to performing the assessment related to blood flow, generating at least one indication that the current stage corresponds to the suitable stage.

Optionally, the one or more programs may include instructions for generating at least one indication of the current stage.

Optionally, the at least one indication of the current stage may indicate a relative rate that a level of fluorescence imaging agent in the at least a portion of the target is increasing or decreasing.

Optionally, the at least one indication may include a graphical indication of the current stage relative to a nominal progression associated with typical movement of fluorescent imaging agent through tissue.

Optionally, generating the at least one indication may be performed in response to a user input.

Optionally, the at least one indication may include a graphical indication.

Optionally, the graphical indication may indicate a relative leveling over time of an amount of fluorescence imaging agent in the at least a portion of the target.

Optionally, the at least one indication may include an audible indication.

Optionally, the blood flow may be assessed in response to a user input received after the at least one indication is generated.

Optionally, the blood flow may be assessed automatically in response to determining that the current stage corresponds to the suitable stage.

Optionally, performing the assessment related to blood flow may include assessing tissue perfusion of the at least a portion of the target.

Optionally, performing the assessment related to blood flow may include quantifying tissue perfusion.

Optionally, the at least one characteristic may include a rate of change of a level of fluorescence intensity.

Optionally, the level of fluorescence intensity may be an average fluorescence intensity.

Optionally, the at least one characteristic may include a standard deviation of fluorescence intensity.

Optionally, comparing the at least one characteristic to predefined criteria may include comparing a current rate of change of a level of fluorescence intensity to a previous rate of change of the level of fluorescence intensity.

Optionally, the fluorescence imaging data may be received from an imager during a medical procedure.

Optionally, the fluorescence imaging data may include endoscopic imaging data or open-field imaging data.

According to various aspects, a non-transitory computer readable storage medium stores one or more programs for execution by one or more processors of a system for guiding assessment related to blood flow, and the one or more programs include instructions for: receiving fluorescence imaging data associated with a fluorescence imaging agent moving through a target, determining at least one characteristic associated with a current stage of movement of the fluorescence imaging agent through the target based on the fluorescence imaging data, comparing the at least one characteristic associated with the current stage to predefined criteria to determine whether the current stage corresponds to a suitable stage for performing an assessment related to blood flow, and in accordance with the current stage corresponding to the suitable stage, performing the assessment related to blood flow in at least a portion of the target based on the fluorescence imaging data.

Optionally, the suitable stage may be associated with a transition from a net increase in fluorescence imaging agent to a reduced net increase, no net change, or a net decrease in fluorescence imaging agent.

Optionally, the one or more programs may include instructions for, prior to performing the assessment related to blood flow, generating at least one indication that the current stage corresponds to the suitable stage.

Optionally, the one or more programs may include instructions for generating at least one indication of the current stage.

Optionally, the at least one indication of the current stage may indicate a relative rate that a level of fluorescence imaging agent in the at least a portion of the target is increasing or decreasing.

Optionally, the at least one indication may include a graphical indication of the current stage relative to a nominal progression associated with typical movement of fluorescent imaging agent through tissue.

Optionally, generating the at least one indication may be performed in response to a user input.

Optionally, the at least one indication may include a graphical indication.

Optionally, the graphical indication may indicate a relative leveling over time of an amount of fluorescence imaging agent in the at least a portion of the target.

Optionally, the at least one indication may include an audible indication.

Optionally, the blood flow may be assessed in response to a user input received after the at least one indication is generated.

Optionally, the blood flow may be assessed automatically in response to determining that the current stage corresponds to the suitable stage.

Optionally, performing the assessment related to blood flow may include assessing tissue perfusion of the at least a portion of the target.

Optionally, performing the assessment related to blood flow may include quantifying tissue perfusion.

Optionally, the at least one characteristic may include a rate of change of a level of fluorescence intensity.

Optionally, the level of fluorescence intensity may be an average fluorescence intensity.

Optionally, the at least one characteristic may include a standard deviation of fluorescence intensity.

Optionally, comparing the at least one characteristic to predefined criteria may include comparing a current rate of change of a level of fluorescence intensity to a previous rate of change of the level of fluorescence intensity.

Optionally, the fluorescence imaging data may be received from an imager during a medical procedure.

Optionally, the fluorescence imaging data may include endoscopic imaging data or open-field imaging data.

BRIEF DESCRIPTION OF THE FIGURES

The invention will now be described, by way of example only, with reference to the accompanying drawings, in which:

FIG. 7 is an illustrative depiction of an exemplary fluorescence imaging system;

DETAILED DESCRIPTION

Figure 1:
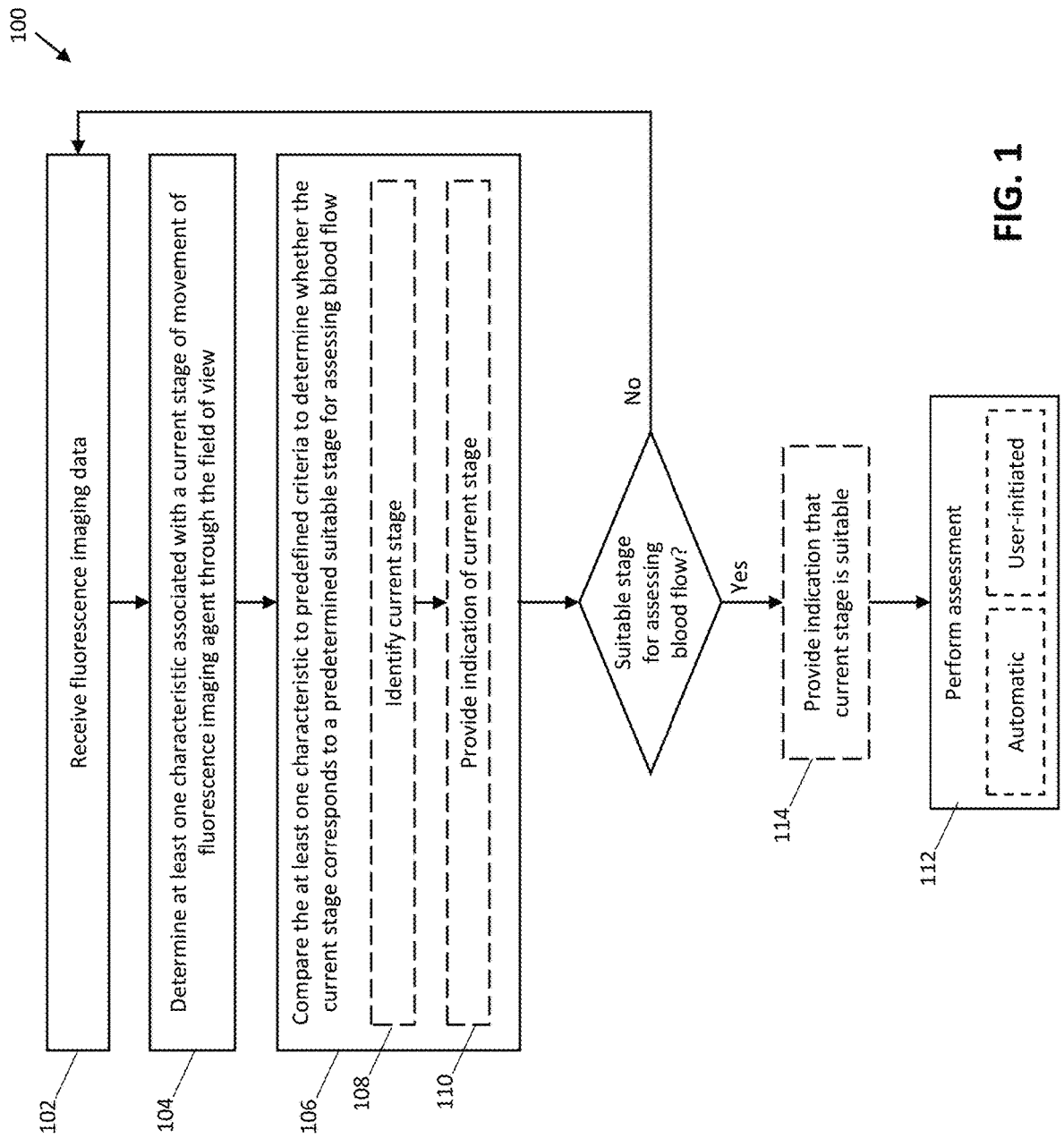
FIG. 1 is an exemplary flow diagram for performing an assessment related to blood flow at a stage of movement of imaging agent that is suitable for assessing the blood flow.

Reference will now be made in detail to implementations and embodiments of various aspects and variations of systems and methods described herein. Although several exemplary variations of the systems and methods are described herein, other variations of the systems and methods may include aspects of the systems and methods described herein combined in any suitable manner having combinations of all or some of the aspects described.

According to various aspects, systems and methods described herein can determine an appropriate time for performing fluorescence imaging based assessments of target tissue as the fluorescence imaging agent moves through the tissue. According to various aspects, guidance can be provided to a medical practitioner, such as via a visual display or an audible indication, to prompt the medical practitioner to initiate an assessment, or the assessment can be automatically performed.

Fluorescence imaging can be used to perform various assessments related to blood flow through tissue, such as quantification of tissue perfusion, using the fluorescence intensity signal captured in fluorescence imaging (includes single images and video frames). Because the movement of fluorescence imaging agent through the tissue is a dynamic process, the timing for performing an assessment can be important. The amount of imaging agent within the field of view will increase over time during what is called an ingress period and will then decrease over time during what is called an egress period. Fluorescence imaging based assessments are best performed when the amount of imaging agent within the tissue of interest has reached a sufficient level, such as near the end of the period of ingress and the beginning of the period of egress. However, the ingress and egress characteristics of the imaging agent bolus depend on various factors, including patient anatomy, patient physiology and comorbidities, and the technique that was used in administering the fluorescence imaging agent. Therefore, the ingress and egress timing may be different based on differences in these factors. As such, it is generally not possible to know a priori when to perform a tissue assessment based on the fluorescence imaging.

Not all medical practitioners who use fluorescence imaging based assessments understand that timing and ingress/egress are factors to be considered. For those who do, assessment timing can be based on the medical practitioner's training and experience in visual interpretation of the fluorescence signal. However, relying on visual perception and practitioner training and experience can lead to inaccurate and inconsistent results, as it can be difficult to visually determine when a fluorescence signal is stable, experience varies from practitioner to practitioner, and the fluorescence response varies from case to case. Some practitioners may rely on fixed delays after the onset of fluorescence detection, but this technique is not accurate as it does not account for variation in patient physiology. Still other practitioners wait until after the fluorescence imaging agent has traversed the tissue and look at the history of the fluorescence signal after the fact to determine the appropriate portion of the imaging sequence to use for the assessment. This technique is more accurate than visually assessing signal stability in real time but is not a real time tool and still relies on practitioner understanding of fluorescence imaging assessment timing.

Systems and methods described herein, according to various aspects, analyze fluorescence images as a bolus of imaging agent traverses the tissue within the field of view to determine an appropriate time to perform assessments of the tissue as the imaging session progresses—i.e., in real time. Guidance can be provided to a medical practitioner for when to perform a blood flow related assessment and/or a blood flow related assessment can be automatically performed at the appropriate time. Thus, analysis of blood flow or blood flow related processes such as tissue perfusion can be performed at the correct time without relying on the training and experience of the practitioner. Further, the analysis can be performed in real time as the imaging agent is passing through the tissue. The systems and methods described herein according to various aspects can provide real time guidance that is systematically generated such that both new and experienced users will be able to consistently perform blood flow related assessments at an appropriate time.

According to various aspects, systems and methods according to the principles described herein can be used for providing imaging based analysis timing guidance for any imaging modality in which the presence of an imaging agent in the tissue of interest is transient, including, for example, lymphatic imaging and nerve imaging.

According to various aspects, fluorescence imaging data that captures the fluorescence signal of fluorescence imaging agent passing through target tissue is received at one or more processors and is analyzed to determine the appropriate time for performing an assessment related to blood flow, such as assessing tissue perfusion of the tissue or assessing blood flow, using the fluorescence signal from the fluorescence imaging agent. One or more characteristics associated with a current stage of the movement of the fluorescence imaging agent through the target tissue can be determined based on the fluorescence imaging data. This can include, for example, determining a measure of fluorescence intensity per unit time and determining changes in the measure over time by comparing a current measure to one or more previous measures. The one or more characteristics associated with currently received imaging data can be compared to predefined criteria to determine whether the current stage is suitable for performing an assessment related to blood flow.

A suitable stage for performing an assessment related to blood flow can be, for example, at or near the end of the period of ingress of fluorescence imaging agent. The end of ingress can be an ideal time to perform an assessment related to blood flow since the fluorescence signal will be strongest and the likelihood that the fluorescence imaging agent has spread throughout the tissue of interest may be greatest. Systems and methods described herein, according to various aspects, can monitor the change in mean fluorescence intensity within the fluorescence imaging frame over time to detect a period at which the change in mean fluorescence intensity levels off after a period of continued increase, which can indicate that the period of ingress is ending. This leveling off after a period of continued increase can be used to identify the current stage as a suitable stage for performing an assessment related to blood flow within the tissue.

Optionally, in accordance with a determination that the current stage is suitable for performing an assessment related to blood flow within the tissue, guidance can be provided to a medical practitioner that the current time is suitable for performing the fluorescence imaging based assessment. The guidance can include a visual display, such as provided on one or more displays, and/or can include an audible cue. Optionally, a visual display is provided throughout the monitoring of the fluorescence imaging signal to provide the medical practitioner with continued guidance regarding the current stage of the movement of the fluorescence imaging agent through the imaged tissue.

Optionally, the medical practitioner may initiate an assessment related to blood flow based on guidance that the time is appropriate for performing the assessment. Optionally, the medical practitioner may command the imaging system or a system communicatively connected to the imaging system to perform a quantitative assessment based on at least a portion of the fluorescence imaging data, such as using a suitable user interface. Optionally, the same system that determines the appropriate time for performing the assessment related to blood flow also performs the assessment.

Assessments can include any analysis (e.g., quantitative) related to blood flow, including blood flow through individual vessels and tissue perfusion, that is performed based on the fluorescence imaging data, and the results can include numerical information and/or visual information. For example, a heat map and/or contour lines indicating levels of tissue perfusion within the field of view can be generated and displayed to the medical practitioner and/or markers indicating relative percentages of tissue perfusion within the field of view can be provided.

Optionally, instead of or in addition to providing guidance to a medical practitioner, the assessment related to blood flow can be automatically performed in response to a determination that the current stage is suitable for performing the assessment. For example, rather than relying on the medical practitioner to request performance of an assessment, the imaging system or a connected system can automatically perform an assessment in response to the determination that the current period of movement of the fluorescence imaging agent through the tissue is suitable for performing the assessment. The results of the assessment may then be provided to the medical practitioner, such as via one or more displays.

As used herein, assessments related to blood flow include assessment of blood flow through blood vessels (vascular blood flow), which can be quantified in terms such as volumetric flow rate (i.e., volume/time) or travel speed (i.e., distance/time), as well as assessment of tissue perfusion, which is distinguished from vascular blood flow in that tissue perfusion defines movement of blood through blood vessels within a tissue volume. More specifically, tissue perfusion relates to the microcirculatory flow of blood per unit tissue volume in which oxygen and nutrients are provided to, and waste is removed from, the capillary bed of the tissue being perfused. Perfusion is associated with nutritive blood vessels (i.e., micro-vessels known as capillaries) that comprise the vessels associated with exchange of metabolites between blood and tissue, rather than larger diameter non-nutritive vessels.

There are many circumstances in which medical practitioners desire to correctly assess vascular blood flow and/or tissue perfusion in tissue. For example, in treating patients with wounded tissue, clinicians must correctly assess vascular blood flow and/or tissue perfusion in and around a wound site, since poor tissue perfusion will have an adverse effect on the healing process. An accurate assessment of vascular blood flow and/or tissue perfusion increases the chances of successful healing of both acute (e.g., surgical) and chronic wounds. The assessment of perfusion dynamics is also important in other clinical applications, such as for example pre-surgical evaluation of patients undergoing plastic reconstruction procedures (e.g., skin flap transfers), or assessment of viability and function of cardiac tissue during cardiac surgery (e.g., coronary artery bypass graft surgery).

Provided below are details of various examples for monitoring the movement of the fluorescence imaging agent through the imaged tissue and determining the appropriate time for performing an assessment related to blood flow through the tissue.

In the following description of the various embodiments, reference is made to the accompanying drawings, in which are shown, by way of illustration, specific embodiments that can be practiced. It is to be understood that other embodiments and examples can be practiced, and changes can be made without departing from the scope of the disclosure.

In addition, it is also to be understood that the singular forms "a," "an," and "the" used in the following description are intended to include the plural forms as well, unless the context clearly indicates otherwise. It is also to be understood that the term "and/or" as used herein refers to and encompasses any and all possible combinations of one or more of the associated listed items. It is further to be understood that the terms "includes, "including," "comprises," and/or "comprising," when used herein, specify the presence of stated features, integers, steps, operations, elements, components, and/or units but do not preclude the presence or addition of one or more other features, integers, steps, operations, elements, components, units, and/or groups thereof.

Certain aspects of the present disclosure include process steps and instructions described herein in the form of an algorithm. It should be noted that the process steps and instructions of the present disclosure could be embodied in software, firmware, or hardware and, when embodied in software, could be downloaded to reside on and be operated from different platforms used by a variety of operating systems. Unless specifically stated otherwise as apparent from the following discussion, it is appreciated that, throughout the description, discussions utilizing terms such as "processing," "computing," "calculating," "determining," "displaying," "generating" or the like, refer to the action and processes of a computer system, or similar electronic computing device, that manipulates and transforms data represented as physical (electronic) quantities within the computer system memories or registers or other such information storage, transmission, or display devices.

The present disclosure also relates to a device for performing the operations herein. This device may be specially constructed for the required purposes, or it may comprise a general purpose computer selectively activated or reconfigured by a computer program stored in the computer. Such a computer program may be stored in a non-transitory, computer readable storage medium, such as, but not limited to, any type of disk, including floppy disks, USB flash drives, external hard drives, optical disks, CD-ROMs, magnetic-optical disks, read-only memories (ROMs), random access memories (RAMs), EPROMs, EEPROMs, magnetic or optical cards, application specific integrated circuits (ASICs), or any type of media suitable for storing electronic instructions, and each coupled to a computer system bus. Furthermore, the computers referred to in the specification may include a single processor or may be architectures employing multiple processor designs for increased computing capability.

The methods, devices, and systems described herein are not inherently related to any particular computer or other apparatus. Various general-purpose systems may also be used with programs in accordance with the teachings herein, or it may prove convenient to construct a more specialized apparatus to perform the required method steps. The required structure for a variety of these systems will appear from the description below. In addition, the present invention is not described with reference to any particular programming language. It will be appreciated that a variety of programming languages may be used to implement the teachings of the present invention as described herein.

FIG. 1 illustrates an exemplary method 100 for tracking the movement of fluorescence imaging agent through tissue within a field of view and performing an assessment related to blood flow at a stage of the movement of the imaging agent that is suitable for assessing the blood flow. Method 100 is performed based on fluorescence images generated by a fluorescence imaging system and can be performed by the fluorescence imaging system or any computing system communicatively coupled to the fluorescence imaging system for receiving fluorescence images from the fluorescence imaging system.

Method 100 can be performed after the administration of a bolus of a fluorescence imaging agent to a patient and based on fluorescence images generated using a fluorescence imager that has tissue of interest of a subject within its field of view. Depending on the procedure, the tissue of interest can be imaged during an invasive procedure, such as a minimally invasive procedure using an endoscopic imager or an open procedure using an open-field imager, or via a non-invasive procedure, such as involving through-the-skin imaging.

At step 102, fluorescence imaging data is received at one or more processors. The fluorescence imaging data can include a time series of fluorescence images (which includes video frames) and can be received as the fluorescence imaging data is generated (i.e., "in real time"). The fluorescence imaging data can be received directly from a fluorescence imager or from any suitable component of a fluorescence imaging system, such as from a camera control unit, or from a system that processes imaging data from the imaging system. The imaging data is received at one or more processors that can be or include one or more processors of the imaging system, including one or more processors of the imager itself, or one or more processors of a computing system that is communicatively connected to the imaging system. Optionally, each fluorescence image frame generated by the fluorescence imager is received at step 102, or a subset (e.g., every other, every tenth, etc.) of the fluorescence image frames generated by the fluorescence imager are received at step 102.

At step 104, the fluorescence imaging data is used to determine at least one characteristic associated with a current stage of movement of the fluorescence imaging agent through the field of view. The at least one characteristic can be indicative of a relative amount of blood flow within the field of view. An example of a suitable characteristic to use for determining the timing for blood flow analysis is the rate of the change in one or more measures of fluorescence intensity over time in the imaging data. A decrease in the rate of change after a period of relatively high rate of change can indicate the end of the ingress period of fluorescence imaging agent movement, which can be a suitable time for performing a blood flow assessment. Determination of this characteristic can include determining a mean fluorescence intensity in a current fluorescence image frame and comparing that current mean fluorescence intensity value to mean fluorescence intensity values from one or more previous frames to calculate the slope of the change over time of the mean fluorescence intensity. Optionally, the at least one characteristic is determined for each fluorescence image frame. The at least one characteristic may be determined for less than each fluorescence image frame. Optionally, the at least one characteristic is determined based on more than one fluorescence image frame. For example, a moving average of mean fluorescence intensity may be used and can be determined by averaging the mean fluorescence intensity of the current frame and a predefined number of preceding frames (e.g., two, five, ten, twenty, etc.), which can help reduce the influence of noise in the fluorescence imaging data.

Another example of a suitable characteristic is the standard deviation of fluorescence intensity values in an image frame. A relatively lower standard deviation that follows a period of higher standard deviation may be associated with fluorescence imaging agent reaching a greater proportion of the tissue within the field of view, which can be a suitable time for performing an assessment related to blood flow. The change in the standard deviation over time could also be a suitable characteristic, with lower rates of change following a period of higher rates of change being associated with stabilization of the amount of fluorescence imaging agent in the field of view, which can be associated with the end of the ingress period.

At step 106, the at least one characteristic determined in step 104 is compared to predefined criteria to determine whether the current stage of the movement of the fluorescence imaging agent through the imaged tissue is suitable for performing an assessment related to blood flow. The comparison can be based upon a current value of a characteristic, such as the current rate of change of the mean fluorescence intensity, as well as on previous values of the characteristic, such as past rates of change of the mean fluorescence intensity. Examples of predefined criteria include whether the characteristic has a positive or negative value, whether the characteristic meets a certain numerical threshold, or whether the characteristic has changed in a particular way.

Optionally, the predefined criteria include a determination that a previous stage of movement of the imaging agent has been achieved. For example, a reduction in the rate of change of a measure of fluorescence intensity in an image frame may trigger a determination that the time is suitable for performing an assessment related to blood flow only if a determination was previously made that an ingress stage had begun. Accordingly, method 100 may include identifying, at step 108, a current stage of the movement of the imaging agent through the tissue, such as one or more stages that precede the stage suitable for performing an assessment related to blood flow. This can include comparing the characteristic(s) determined at step 104 (alone or in combination with previously determined characteristic values) to one or more predefined criteria associated with each stage of movement to determine a current stage. For example, an ingress stage can be determined by detecting a frame-to-frame increase in mean frame fluorescence intensity that is above a first threshold value, and once the ingress stage has been determined, the frame-to-frame change in mean frame fluorescence intensity can be compared to a second threshold value to detect when the level of increase drops below the threshold, which can indicate that the fluorescence intensity in the field of view is stabilizing—a suitable time to perform the blood flow assessment.

The suitable stage can be associated with a transition from a net increase in fluorescence imaging agent (an ingress or ingress advance stage) to a reduced net increase (an ingress retreat stage), no net change (a peak stage), or a net decrease in fluorescence imaging agent (an egress or egress advance stage). For example, a suitable stage may begin at or around a time that the rate of increase in imaging agent in the field of view (e.g., as determined by a measure of the fluorescence intensity in an image frame) reaches a maximum (or shortly thereafter) and may continue until the rate of change of a decrease in the imaging agent in the field of view reaches a threshold value associated with the egress stage. Optionally, the suitable stage is associated with the peak in imaging agent in the field of view, such as determined by zero or relatively little change in imaging agent from one frame to the next.

Method 100 can include providing one or more indications, such as a visual indication, of a current stage of the movement of the fluorescence imaging agent through the tissue at step 110. The indication can indicate one or more discrete stages of the movement of the imaging agent and can indicate a relative degree of imaging agent within the field of view. For example, an indication of the frame-to-frame increase in mean frame fluorescence can be provided along with an indication that the current stage is the ingress stage.

If the current stage is not suitable for performing the blood flow assessment as determined at step 106, then method 100 returns to step 102 for receiving and analyzing further fluorescence imaging data. If the current stage is suitable, then the assessment related to blood flow is performed at step 112. The assessment can include any suitable analysis or analyses related to blood flow (e.g., assessment of vascular blood flow and/or assessment of tissue perfusion) that is based on the fluorescence imaging data and can be based on an analysis of a current fluorescence imaging frame, alone, or also based on one or more previous fluorescence imaging frames.

Assessments may be performed based on fluorescence intensity pixel data within a field of view of the fluorescence imaging frames or may be performed on a region of interest within a field of view, such as a user-selected field of view. Where a region of interest is selected by a user, blood flow related assessment timing determinations can be based on only the fluorescence intensity signals within the region of interest.

An assessment can be a user-initiated assessment or an automatic assessment. An automatic assessment may be performed in response to the determination that the current stage is a suitable stage for performing the assessment without requiring a user command. An indication may be provided to the medical practitioner to indicate that the current stage is a suitable stage and that the blood flow assessment is being automatically performed. The results of the assessment may then be provided to the user.

For user-initiated assessments, the medical practitioner may be provided with one or more indications that a suitable stage has been reached at step 114, and the medical practitioner may then provide a command in response to perform the blood flow assessment using any suitable user interface or the medical practitioner may then manually perform a blood flow assessment. For example, a visual display of the current stage of fluorescence imaging agent movement may indicate to the medical practitioner that the current stage is suitable for performing an assessment related to blood flow and the medical practitioner may respond by commanding the imaging system or other system communicatively coupled to the imaging system to perform an assessment of, say, tissue perfusion in the current fluorescence image frame or a recent subset of frames, or the medical practitioner may respond by manually performing a visual blood flow assessment of the current fluorescence image frame and/or commanding the system to save the current fluorescence image frame for later assessment or comparison. Optionally, the one or more indications may be provided in response to a user input, such as a user request to view the current stage of the imaging agent flow through the target tissue.

Figure 2A:
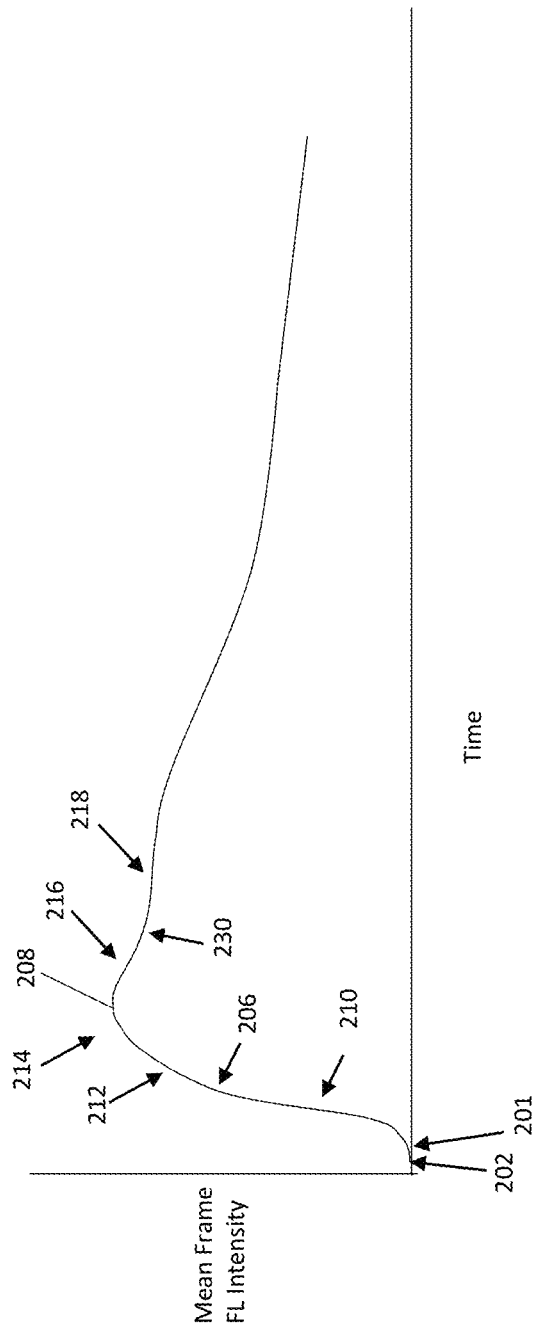
FIG. 2A is a graph of mean frame fluorescence intensity over time for an exemplary imaging session.
Figure 2B:
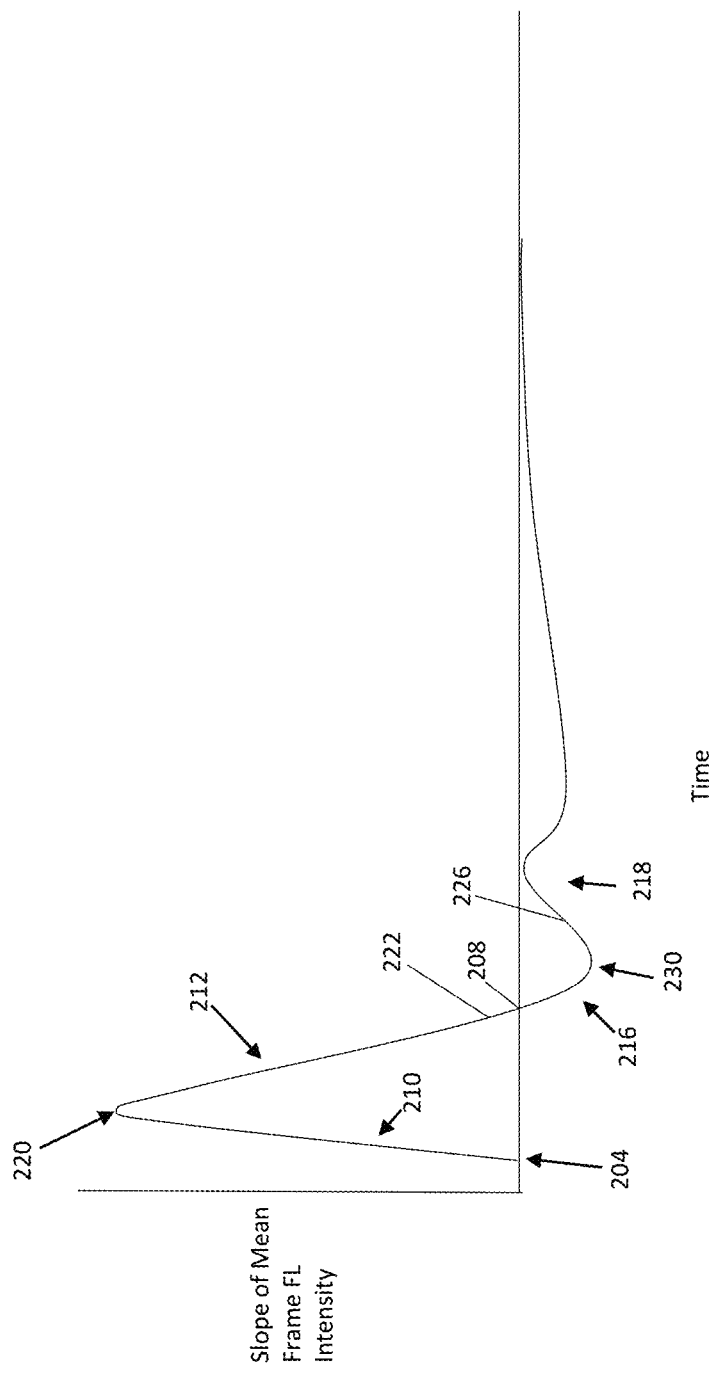
FIG. 2B is a graph of the slope of the graph of FIG. 2A, showing exemplary rates of change of mean frame fluorescence intensity over time.

FIGS. 2A and 2B illustrate exemplary characteristics of the fluorescence intensity signal associated with the movement of fluorescence imaging agent through a field of view that can be utilized for determining the stages of the movement and/or the appropriate timing for performing an assessment related to blood flow. FIG. 2A is a graph of mean frame fluorescence intensity over time for an exemplary imaging session in which a bolus of fluorescence imaging agent has been provided to a subject. The x-axis corresponds to time and the y-axis corresponds to the mean fluorescence intensity of each frame. FIG. 2B is the derivative of the graph of FIG. 2A, showing the rates of change of the mean frame fluorescence intensity over time.

The mean frame fluorescence intensity, which can be calculated by averaging the fluorescence intensities in a frame, starts out at time 202 at a low value, such as close to zero, indicating that the imaging agent has not yet entered the field of view. Around time 201, the mean fluorescence intensity begins increasing as imaging agent enters the field of view. This is followed by a rapid rise in the fluorescence intensity over time, which can be considered an "ingress advance" stage 210. The increase in fluorescence intensity reaches an inflection point at time 206 at which the rate of ingress slows, which can be considered the beginning of an "ingress retreat" stage 212. A peak is reached at time 208 when the amount of fluorescence intensity within the field of view stabilizes, which can be considered a "peak stage" 214. The peak stage 214 can be a suitable stage for performing an assessment related to blood flow because it is typically associated with imaging agent reaching the greatest proportion of the tissue within the field of view and/or reaching the greatest concentration within the tissue. Since the assessment related to blood flow based on the fluorescence imaging can be based on the fluorescence intensity, maximum fluorescence intensity across the field of view may provide the most accurate results. Thus, the peak stage 214 may be the optimal time to perform the assessment. Since the change in the mean intensity before and after the peak 208 can be relatively low, the peak stage 214 (i.e., the stage suitable for performing an assessment related to blood flow) can encompass a period of time before and/or after the peak 208.

After the peak 208, the net amount of imaging agent within the field of view decreases over time, which can be considered an "egress advance" stage 216. The level of decline may begin flattening out, such as at time 230, and it may take some time for the imaging agent to be cleared from the tissue by the blood flow in the tissue. This stage can be considered the "egress retreat" stage 218.

The various transition points from the beginning of ingress ("ingress advance"), to the slowing of ingress ("ingress retreat"), to the peak stage, to the beginning of egress ("egress advance"), and to the slowing of egress ("egress retreat") can be seen in the derivative (i.e., slope) graph shown in FIG. 2B. These transition points can form the basis of the predetermined criteria used according to method 100 to determine the stages of the movement of the imaging agent through the tissue within the field of view. The ingress advance stage 210 may be determined according to step 108 of method 100 based on an increase above a threshold of the rate of change of the mean frame fluorescence intensity at time 204. The ingress retreat stage 212 may be determined according to step 108 by a reduction from a maximum 220 of the rate of change of the mean fluorescence intensity at time 206. The peak stage 214 may be determined according to step 106 based on the rate of change of mean frame fluorescence intensity dropping below a threshold value 222 and can include the time that the rate of change is zero—the peak time 208. The egress advance stage 216 can be determined according to step 108 by the rate of change dropping below a negative threshold value. The egress retreat stage 218 can be determined according to step 110 by the rate of change increasing above a minimum value 226.

Figure 3:
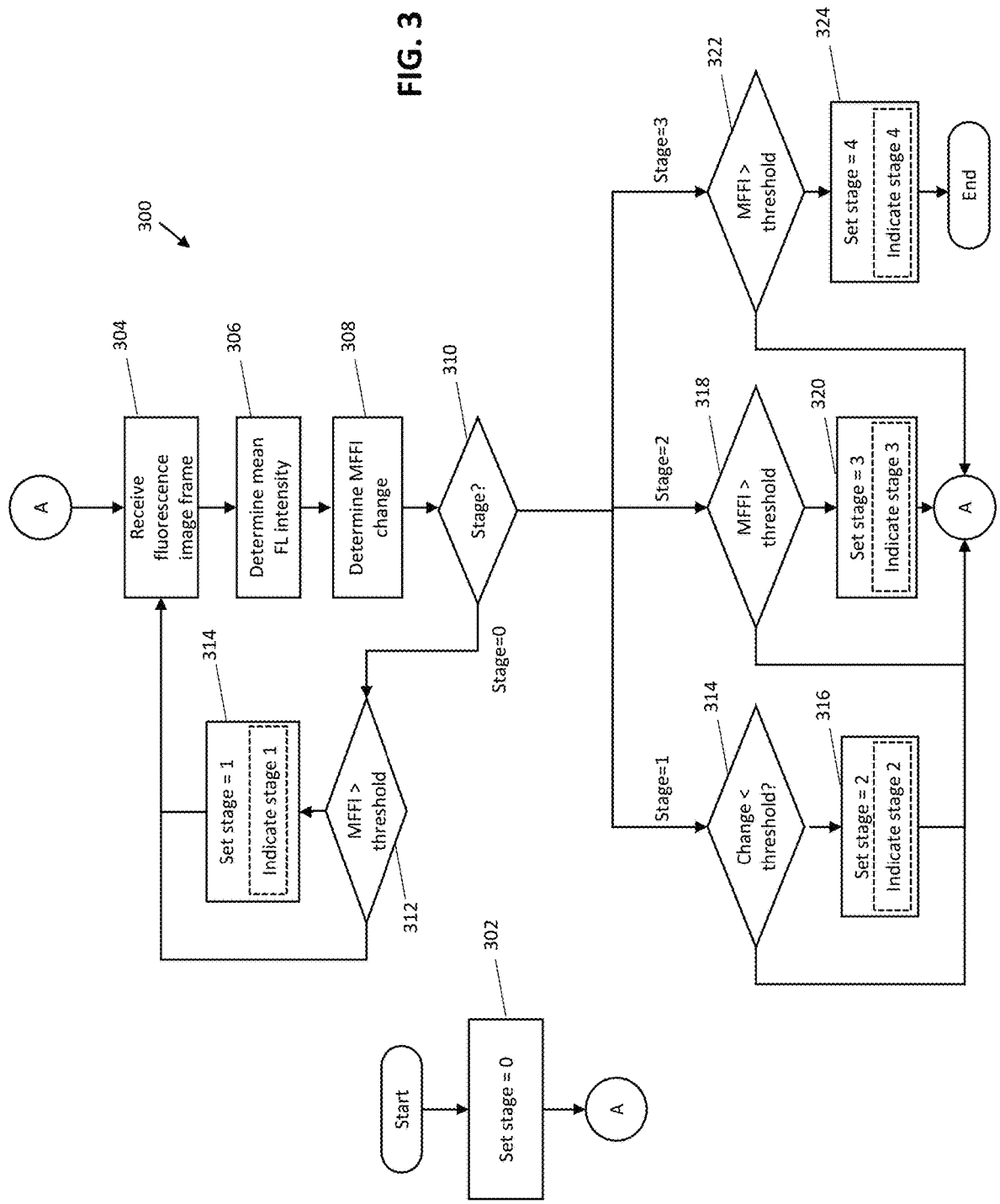
FIG. 3 is a flow diagram for an exemplary method for determining the stages of the movement of fluorescence imaging agent through a field of view.

FIG. 3 is a flow diagram of a method 300 for determining the stages of the movement of fluorescence imaging agent through a field of view. Method 300 can determine five discrete stages of an "ideal graph" of the movement of the fluorescence imaging agent, but the principles described below can be extended to greater or fewer stages. Method 300 can be used for triggering the visual indications of FIG. 4, which are described further below, and/or for determining whether the current stage corresponds to a suitable stage for performing an assessment related to blood flow according to steps 102-106 of method 100. Method 300 may be performed after a bolus of fluorescence imaging agent has been administered to a subject and upon commencing the fluorescence imaging of target tissue of the subject.

At the beginning of method 300, at step 302, the stage of the movement of the fluorescence imaging agent through the tissue is set to stage 0, which corresponds to the bolus of fluorescence imaging agent not yet reaching the field of view. At step 304, a fluorescence imaging frame is received from a fluorescence imager (e.g., directly from the imaging sensor or image generating circuitry or from an imaging system). At step 306, a first characteristic associated with a current stage of movement of fluorescence imaging agent through the field of view, which in this example is the mean frame fluorescence intensity (MFFI), is determined. However, any other suitable measure of fluorescence intensity in the frame can be used, including for example a moving average of mean frame fluorescence intensity of a certain size (e.g., 5 frames, 10 frames, etc.). MFFI is referred to below but it is to be understood that any other suitable measure can be used. At step 308, a second characteristic is determined, which in this example is a change over time of MFFI, which is determined based on the current MFFI from step 306 and the MFFI from one or more previous frames. Optionally, the change in MFFI is simply the difference in MFFI from the immediately preceding frame. The change in MFFI is referred to below as $\Delta$MFFI.

At step 310, the current stage is checked. If the current stage is stage 0, then method 300 continues to step 312 in which the $\Delta$MFFI is compared to a threshold value (e.g., 0.05 8-bit digital numbers ("DNs") of increase, though higher or lower bit digital numbers could be used instead) to determine whether the change in MFFI is indicative of the bolus of fluorescence imaging agent moving into the field of view. The $\Delta$MFFI may be used instead of the MFFI itself since there may be some fluorescence signal from residual imaging agent in the field of view due to a previous bolus. If the $\Delta$MFFI is above the threshold, then at step 314 the stage may be set to stage 1, corresponding to ingress and a relatively rapid frame-to-frame rise in the fluorescence signal. Optionally, one or more additional checks are performed before setting the stage to stage 1. For example, a consistent positive $\Delta$MFFI over a predetermined period of time or predetermined number of frames may be required before the stage is changed to stage 1. Optionally, step 312 can include providing an indication that the current stage is stage 1, such as via a graphical display. If the $\Delta$MFFI is not above the threshold, then the stage remains at stage 0.

Method 300 then returns to steps 302-306 for receiving and processing the next fluorescence imaging frame. At step 310, if the stage is set to 1, then method 300 proceeds to step 314 in which the $\Delta$MFFI for the current frame is compared to a threshold value (e.g., 0.5 DNs of increase) that is associated with a decrease in the frame-to-frame rise in the fluorescence signal, which can correspond to an end of what may be considered the ingress stage. In other words, the threshold value may correspond to a continued increase but leveling off of the increase in fluorescence signal. If the $\Delta$MFFI is above the threshold, indicating a continued relatively high frame-to-frame increase in fluorescence signal, then the stage remains at stage 1 and the method returns to step 302. If the $\Delta$MFFI has dropped below the threshold, then the stage is set at step 316 to stage 2, which can be the peak stage. An indication that the current stage is stage 2 can also be provided, such as on a display. Optionally, an indication may be provided that a suitable stage for performing an assessment related to blood flow has been reached.

In stage 2, the MFFI may increase more slowly than in stage 1 until it reaches a peak at which point the MFFI will begin decreasing.

Method 300 then returns to steps 302-310. If at step 310 the stage is determined to be stage 2, the ΔMFFI is compared to a threshold value (e.g., 0.05 DNs of decrease) at step 318 to determine whether the peak stage (stage 2) has ended. The peak stage may encompass the peak fluorescence signal as well as some period of decrease in the fluorescence signal after the peak. Thus, the threshold used for step 318 may be set to allow for some decrease in fluorescence signal in stage 2 associated with the beginning of the egress stage but yet still trigger a change to stage 3 once the fluorescence signal begins dropping more quickly. If the ΔMFFI meets the threshold (i.e., is a high enough decrease) then the stage is set at step 320 to stage 3, which can correspond to the egress stage in which the MFFI decreases from frame to frame. An indication of this change in stage can also be provided. Optionally, an indication may be provided that it is no longer suitable to perform an assessment related to blood flow, which can include ceasing to display an indication that the time is suitable for performing the assessment. If, however, the ΔMFFI does not meet the threshold at step 318, then the stage remains stage 2 and the method 300 returns to step 302.

Method 300 then returns to steps 302-310 for the next fluorescence frame. If the stage is stage 3 at step 310, then the ΔMFFI is compared at step 322 to another threshold that may be associated with a slowing of the rate of decrease in MFFI. If the ΔMFFI meets the threshold in step 322, the stage is set to stage 4 at step 324. An indication of this change may be provided. Stage 4 may correspond with a residual stage in which the reduction in the fluorescence signal has slowed as the fluorescence agent is slowly cleared from the tissue. Once the stage is set to stage 4, which is the final stage in this example, method 300 ends. If the ΔMFFI does not meet the threshold at step 322, then the method returns to step 302

Figure 4:
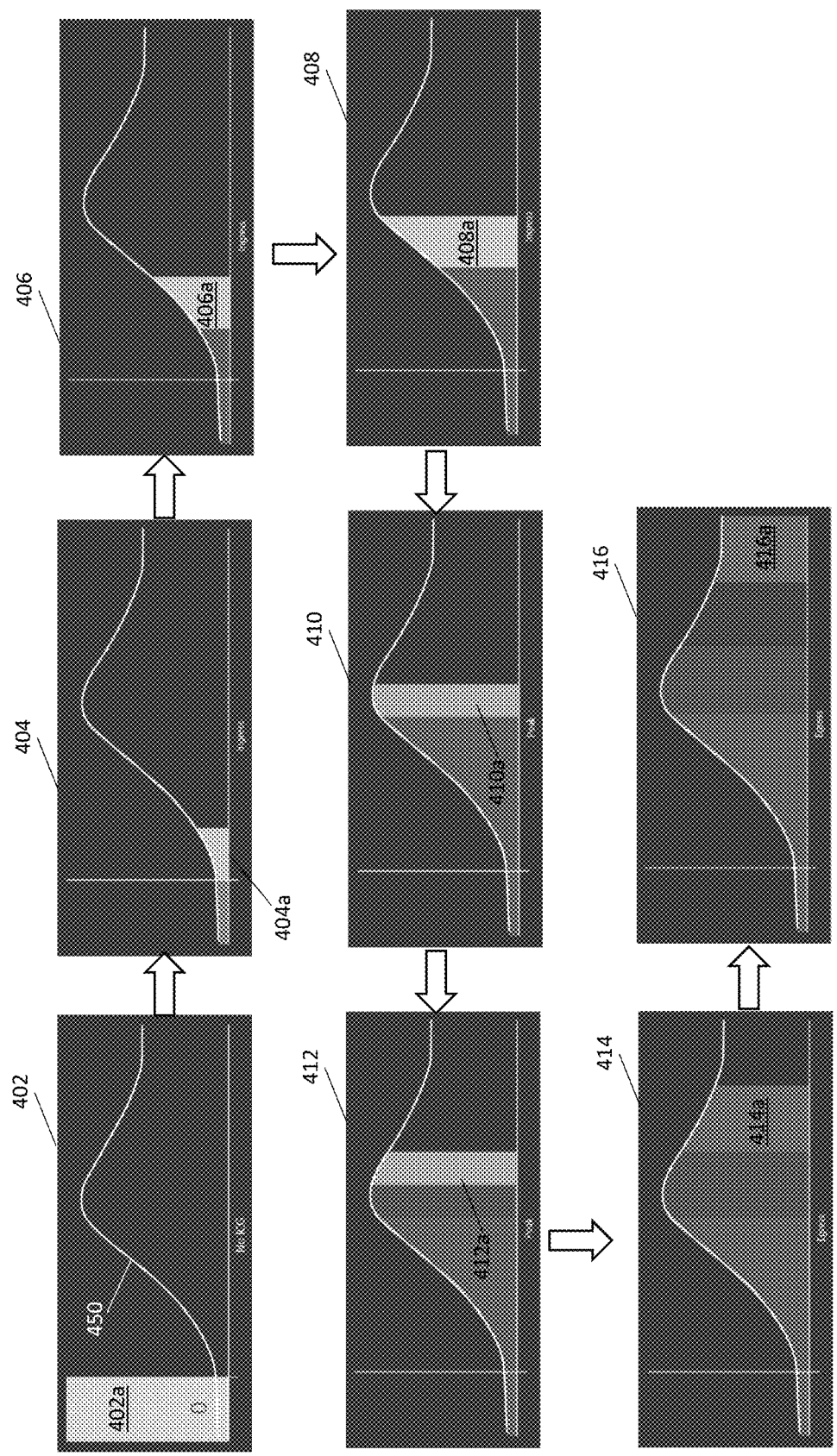
FIG. 4 illustrates exemplary ideal graph visual indications that can be displayed to indicate the stage of movement of the fluorescence imaging agent over time.

FIG. 4 illustrates exemplary "ideal graph" visual indications 402-416 that can be displayed to indicate the stage of movement of the fluorescence imaging agent over time, such as determined via method 300. The visual indications indicate the stages via step-wise progress along an ideal curve 450 that provides a graphical indication of a nominal fluorescence intensity signal over time as a bolus of fluorescence imaging agent moves through target tissue.

The first visual indication 402 can be provided when first detecting a fluorescence signal (e.g., a signal that is above a near zero noise threshold). A bar 402a may be displayed to indicate that the onset of fluorescence intensity is being verified, as discussed further below. Upon verifying the onset of fluorescence intensity, the next visual indication 404 includes a portion 404a under the curve 450 filled in to indicate that the ingress stage has begun.

As the ingress stage progresses, visual indications 406 and 408 illustrate further progress of ingress and may be displayed after predetermined periods of time have elapsed during the ingress stage and/or in response to determining that one or more characteristics of the fluorescence signal meet one or more predefined criteria. For example, portion 406a under the curve 450 in visual indication 406 may be displayed to indicate a stage of ingress advance and may be triggered based on determining that the rate of increase of the fluorescence intensity in the frames has reached a threshold value. The portion 408a under the curve in visual indication 408 can be displayed to indicate a stage of ingress retreat and may be triggered based on the rate of increase of the fluorescence intensity leveling off.

Visual indication 410 can indicate that the peak stage of the fluorescence imaging agent movement has been reached. The portion 410a under the curve 450 in visual indication 410 may indicate to the user that the time is suitable for performing the blood flow assessment. Visual indication 410 may be displayed upon determining, for example, that the rate of change of mean frame fluorescence intensity has dropped below a threshold value.

Visual indication 412 may provide an indication via filled-in portion 412a of curve 450 that egress has begun but that the time is still suitable for performing the blood flow assessment. Visual indication 412 may be displayed in response to determining that the rate of change in the fluorescence intensity has dropped below zero (or some other threshold value).

Visual indication 414, which includes filled-in portion 414a, may indicate that the egress advance stage has begun and may be triggered by the rate of change of fluorescence intensity achieving a threshold negative value. Visual indication 414 may indicate to the user that the suitable stage for performing blood flow assessment has passed. Visual indication 416 may indicate the ingress retreat stage via portion 416a and may be triggered by the rate of change of fluorescence intensity rising above a negative threshold value.

Figure 5:
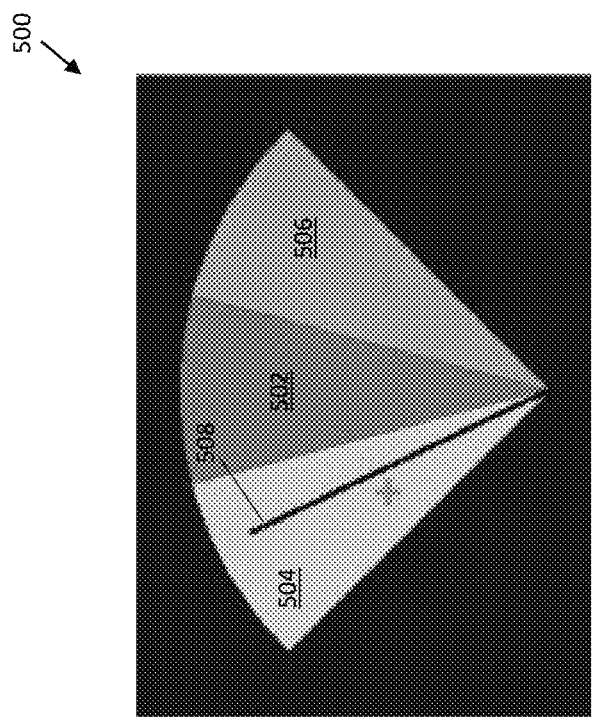
FIG. 5 illustrates an exemplary graphical indicator that can be used for indicating the current stage and the suitable stage for performing assessments of blood flow.

FIG. 5 illustrates an exemplary graphical indicator 500 that can be used for indicating the current stage and the suitable stage for performing assessments related to blood flow. Graphical indicator 500 can be displayed to a user during a fluorescence imaging session to provide real time visual guidance indicating the current stage of the movement of the bolus of imaging agent through the tissue being imaged and can provide an indication to the user that a current stage is suitable for performing a blood flow related assessment, according to the principles discussed above.

Indicator 500 can indicate both the stage of movement of bolus of imaging agent and also the rate of increase/decrease of the fluorescence signal within the field of view. Indicator 500 includes a peak stage region 502 located between an ingress stage region 504 and an egress stage region 506. An indicator needle 508 moves between the three regions based on the determinations of the current stage, as discussed further below. For example, the needle 508 as depicted in FIG. 5 indicates that the current stage is the ingress stage. The center position of the needle 508 (when the needle 508 is vertical) is associated with zero change in fluorescence signal from frame to frame. Positions to the left of center indicate a positive rate of change, which is associated with ingress, while positions to the right of center indicate a negative rate of change, which is associated with egress. The indicator needle 508 moves further to the left or right depending on the magnitude of the rate of change of the fluorescence signal. Thus, the needle 508 may move from a position in the ingress stage region 504 during ingress and will move toward the center as ingress tapers off, eventually moving to the center position when the fluorescence signal reaches its peak value. The needle 508 will then move toward the right as the fluorescence signal begins decreasing from frame to frame, eventually reaching the egress stage region 506. Thus, the needle 508 may indicate both the current stage as well as a relative rate that a level of fluorescence imaging agent in the target tissue is increasing or decreasing. The ingress stage region 504 and egress stage region 506 can be used to indicate that the time is not suitable for performing a blood flow assessment and to indicate information about the stability of the fluorescence signal. The peak stage region 502 indicates that the time is suitable for performing a blood flow assessment.

FIGS. 6A-6F illustrate an exemplary method 600 for driving the needle 508 of graphical indicator 500 of FIG. 5. Method 600 can be used to indicate discrete stages of the movement of a bolus of imaging agent through imaged tissue and can also be used to show relative degrees of increase and decrease in fluorescence signal within the discrete stages. Method 600 is not limited to use for graphical indicator 500 of FIG. 5 but, rather, can be used to drive any other suitable graphical indicator.

Figure 6A:
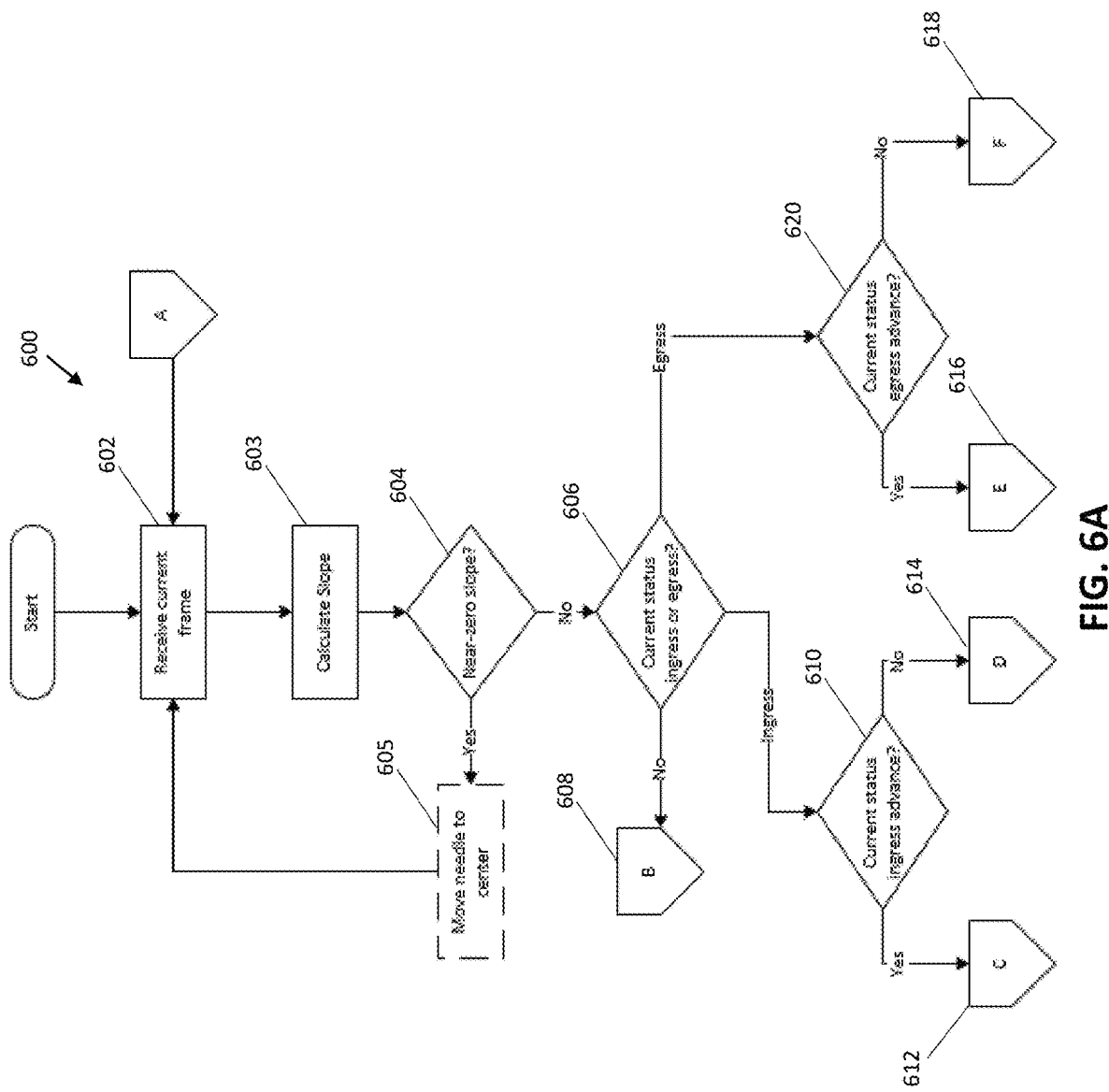
FIGS. 6A-6F illustrate an exemplary method for driving a graphical indicator that indicates the stages of movement of fluorescence imaging agent through a field of view.

Looking first at FIG. 6A, at step 602, a current fluorescence imaging frame is received, such as from an imager or an imaging system. Then, at step 603, a slope of change in mean frame fluorescence intensity is determined for the current fluorescence imaging frame. The slope can be a frame to frame slope determined by subtracting the current mean intensity from the mean intensity of the previous frame or a moving average slope that takes into account the mean intensity of several previous frames. The slope may determined according to the following:

$$\text{Slope} = \frac{\sum_{x=n}^{q} f(x)}{q} - \frac{\sum_{x=n-1}^{q} f(x)}{n}$$

where:
x: frame number
n: current frame
q: queue size
f(x): average intensity of frame x In order to reduce slope value fluctuation and smooth the slope value changes, a moving average technique is implemented using the queue size value, which is the number of frames averaged. Thus, for a queue size of 30, the slope is determined by subtracting the average of the mean intensity of the previous 30 frames from the average of the mean intensity of the current frame and previous 29 frames. Any queue size can be used.

At step 604, the slope determined in step 603 is compared to a near-zero threshold value intended to filter out fluctuations caused by noise. If the slope is near zero (e.g., the absolute value is below a near-zero threshold, such as 0.01 or 0.001), then the needle may be moved to the center at step 605 if not already there and method 600 returns to step 602. If the slope is above the near-zero threshold, then a check is made whether the current status is ingress or egress at step 606. If the current status is not ingress or egress, which may be the case when the bolus of imaging agent first reaches the field of view and ingress has not yet been determined, then a process for detecting ingress or egress is performed at step 608.

Figure 6B:
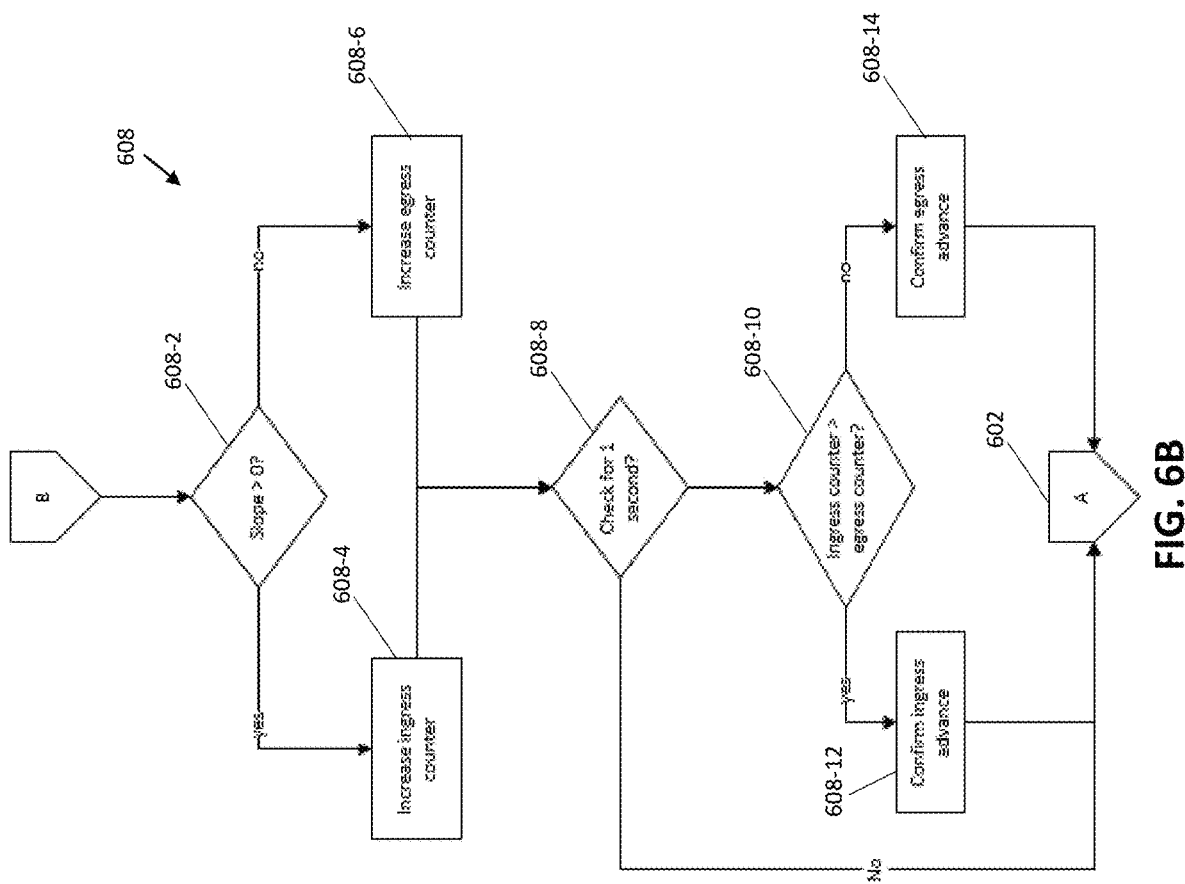

The ingress/egress detection process performed at step 608 is illustrated in FIG. 6B. At step 608-2, a check is made whether the slope determined in step 602 is positive. If the slope is positive, then an ingress counter is increased at step 608-4. If the slope is negative, then an egress counter is increased at step 608-6. In either case, a check is made at step 608-8 whether the counters have been incremented for at least a threshold amount of time (e.g., 1 second). If not, the process returns to step 602 of FIG. 2A. If the counters have been incremented for at least the threshold time, then the determination is made at step 608-10 which counter is greater. If the ingress counter is greater, then the ingress advance stage is confirmed at step 608-12. If the egress counter is greater, then the egress advance stage is confirmed at step 608-14. The process then returns to step 602.

Figure 6C:
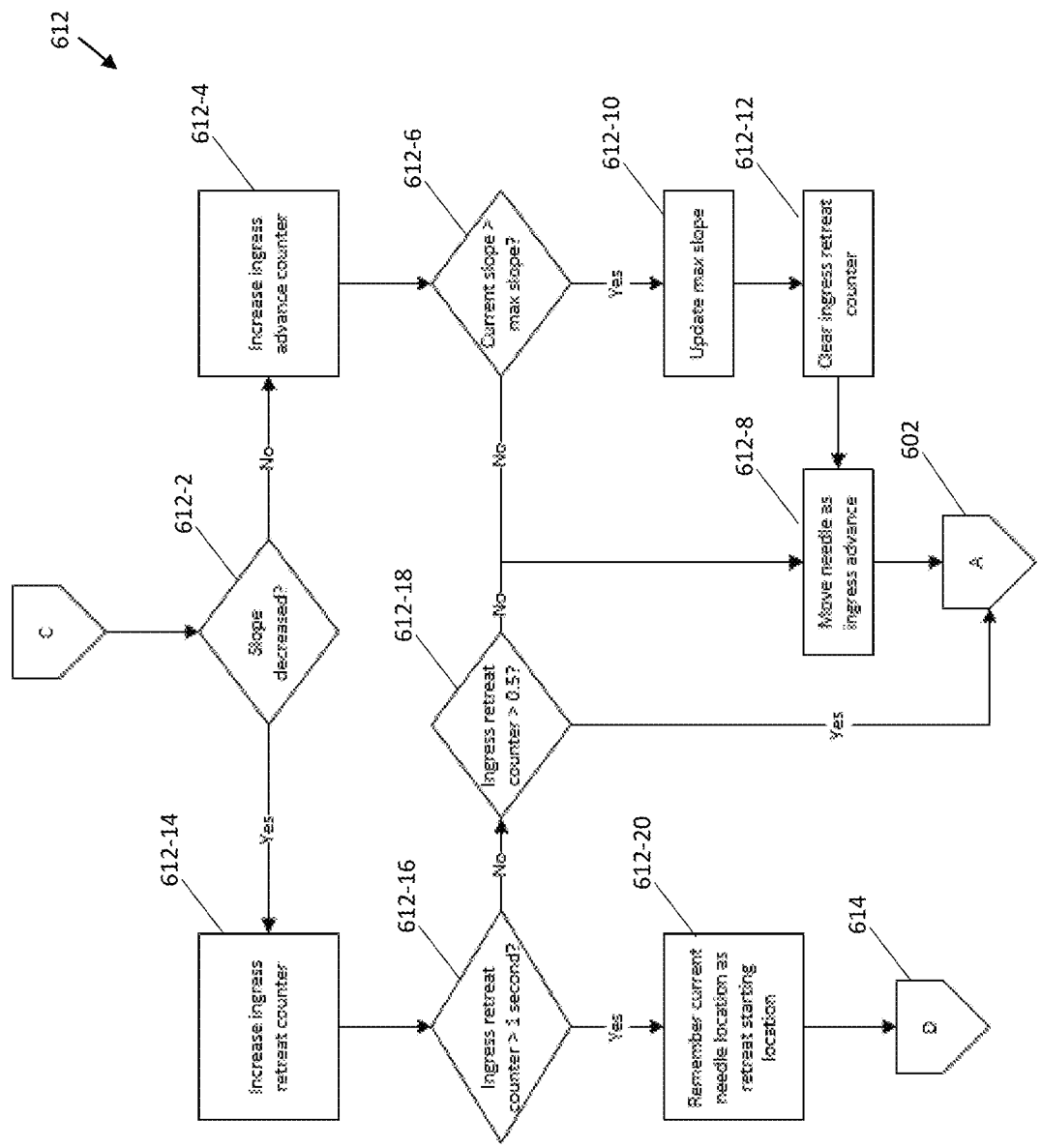

Returning to step 606 of FIG. 6A, if the current status is ingress then a check is made whether the current stage is ingress advance at step 610. If the status is ingress advance, then the needle is moved according to an ingress advance process at step 612, which is illustrated in FIG. 6C. At step 612-2 in FIG. 6C, the current slope is compared to a slope from a previous frame to determine whether the slope has decreased. If the slope has not decreased, then an ingress advance counter is increased at step 612-4. Then, a check is made at step 612-6 whether the current slope is greater than a maximum slope. If not, then the needle is moved according to an ingress advance process at step 612-8.

The needle may be moved at step 612-8 at a rate sufficient for the needle to reach the ingress stage region 504 of indicator 500 within a predetermined period of time that may be selected according to an estimate of the typical amount of time that a period of ingress advance may last. The predetermined period of time can be, for example, about five seconds. Optionally, the needle can move according to the ingress advance movement at the same speed regardless of the value of the slope as long as the slope is the same as or greater than the previous slope. Optionally, the speed of movement of the needle is based at least in part on the value of the slope.

Returning to the check at step 612-6, if the current slope is greater than the maximum slope, then the maximum slope is updated to the current slope at step 612-10, the ingress retreat counter is cleared at step 612-12, and then the needle is moved according to the ingress advance process of step 612-8 described above.

Returning to step 612-2, if the slope has decreased, then an ingress retreat counter is increased at step 612-14. Then a check is made at step 612-16 whether the ingress retreat counter is greater than a first threshold, such as 1 second. If the ingress retreat counter is not greater than the first threshold, then a check is made at step 612-18 whether the ingress retreat counter is greater than a second, lower, threshold. If the ingress retreat counter is greater than the second threshold, then the process returns to step 602 of FIG. 2A. If the ingress retreat counter is not greater than the threshold, then the needle is moved according to the ingress advance process of step 612-8 described above.

Returning to step 612-16, if the ingress retreat counter is greater than the first threshold, the current needle location is stored as the retreat starting location at step 612-20. The needle is then moved according to an ingress retreat process in step 614. The ingress retreat process is shown in FIG. 6D.

Figure 6D:
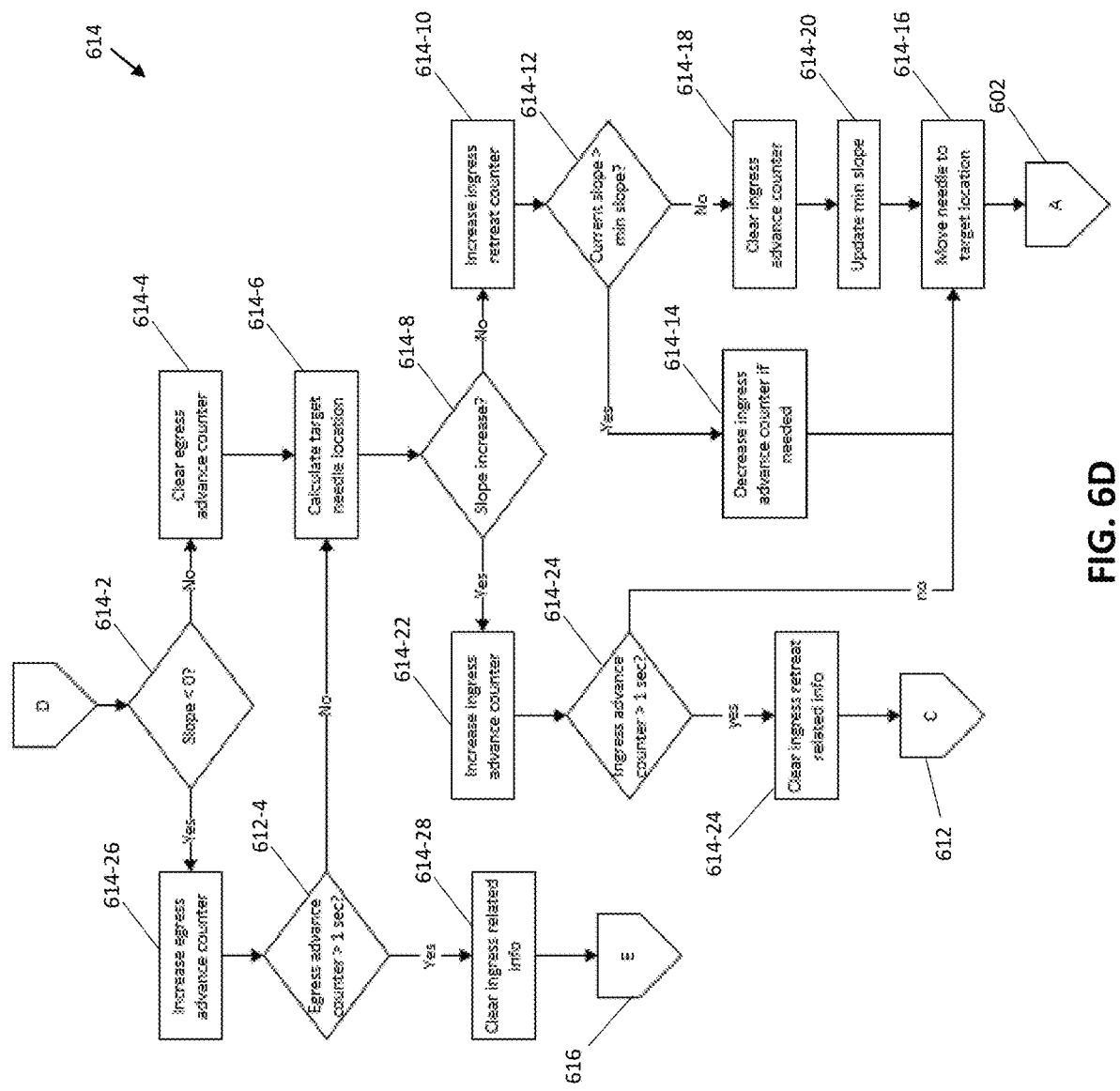

Turning to the ingress retreat process in FIG. 6D, in step 614-2 the slope is checked to determine whether the slope has a negative value. If the slope is positive, then an egress advance counter is cleared at step 614-4 and a target needle location is calculated at step 614-6. The target needle location may be calculated according to the following formula:

$$x = \left(ns + \frac{cs}{ms} * (rs - ns)\right)\pi$$

where:
- x: target needle location (angle in radians measured counterclockwise from horizontal-right),
- ns: needle start location (with center of the slope indicator=0.5),
- cs: current slope,
- ms: max slope value for the ingress mode,
- rs: needle location when ingress retreat started Thus, during the ingress retreat mode, the needle moves based on the ratio of the current slope value to the maximum slope value in the ingress advance mode. The needle start location is determined in step 612-20 in FIG. 6C.

Once the target needle location is calculated, a check is performed at step 614-8 whether the slope has increased relative to the previous slope. If the slope has not increased, then an ingress retreat counter is increased at step 614-10. Then the current slope is compared to a minimum slope at step 614-12. If the current slope is greater than the minimum slope, then the ingress advance counter may be decreased at step 614-14, and in step 614-16, the needle is moved to the target location calculated in step 614-6. Returning to step 614-12, if the current slope is not greater than a minimum slope, then the ingress advance counter is cleared at step 614-18, the minimum slope is updated to the current slope at step 614-20, and then the needle 508 is moved to the target location in step 614-16. The needle 508 may move into the peak stage region 502, which can indicate to the user that the suitable stage for performing an assessment related to blood flow has been reached. The stage may be suitable as long as the needle remains in the peak stage region 502.

Returning to step 614-8, if the slope has increased, the ingress advance counter is increased at step 614-22. Then a check is performed at step 614-24 whether the ingress advance counter is greater than a threshold (e.g., one second). If the ingress advance counter is not greater than the threshold, then the needle is moved to the target location at step 614-16. If the ingress advance counter is greater than the threshold, then the ingress retreat related information, such as the target needle location, is cleared at step 614-24 and the method returns to step 612 of FIG. 6C.

Returning to step 614-2, if the slope has a negative value, an egress advance counter is increased at step 614-26 and then a check is performed whether the egress advance counter is greater than a threshold, such as 1 second. If the egress advance counter has not yet reached the threshold, then the process turns to the calculation of the target needle location at step 614-6, as discussed above. Once the egress advance counter reaches the threshold, indicating consecutive negative slopes, ingress related information is cleared at step 614-28 and the needle is moved according to an egress advance mode in step 616, which is shown in more detail in FIG. 6E.

Figure 6E:
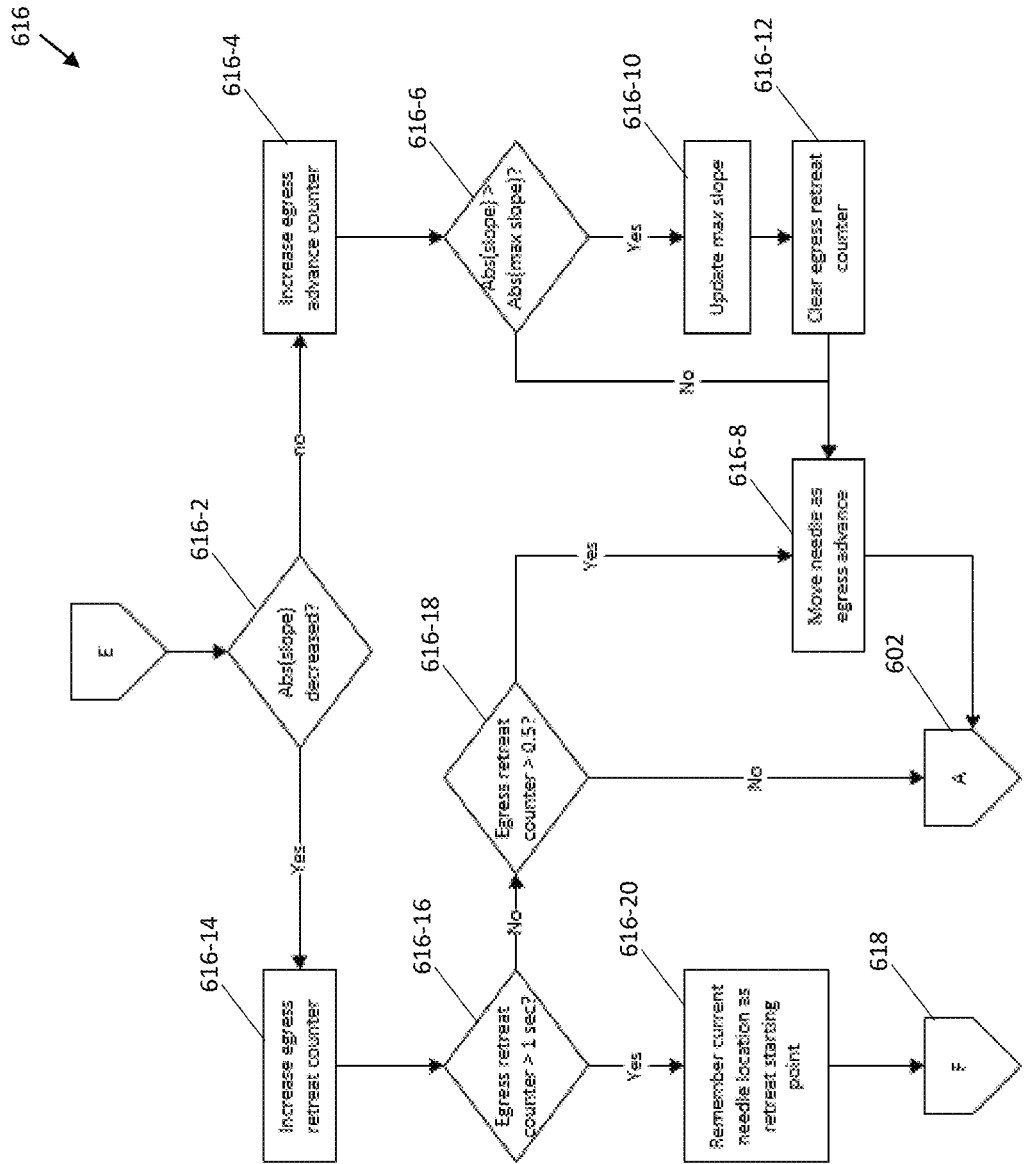

FIG. 6E illustrates step 616—the movement of the needle in an egress advance mode. At step 616-2 a check is made whether the absolute value of the slope has decreased. If it has not, then an egress advance counter is increased at step 616-4. Then a check is made whether the absolute value of the slope is greater than the absolute value of a maximum slope at step 616-6. If the absolute value of the slope is not greater than the absolute value of a maximum slope, then the needle is moved according to an egress advance process in step 616-8.

The egress advance movement process of step 616-8 can be similar to the ingress advance movement process of step 612-8 discussed above. The needle may be moved in fixed increments selected so that the needle reaches the egress stage region 506 of indicator 500 within a time that the egress advance stage is expected to last according to typical timing. Since the egress advance mode may last for a shorter time than the ingress advance process, the needle movement rate may double relative to the ingress advance needle movement rate. So, for example, where the needle is moved in the ingress advance stage at a rate sufficient to move the needle to the ingress stage region of the indicator within 5 seconds, the needle may be moved in the egress advance stage at a rate sufficient to move the needle to the egress stage region of the indicator within 2.5 seconds. These times are merely exemplary and it is to be understood that the timing can be selected according to the particular indicator used and/or the particular imaging session.

If the absolute value of the slope is greater than the absolute value of a maximum slope (step 616-6), then the maximum slope is updated to the current slope at step 616-10, the egress retreat counter is cleared at step 616-12, and then the needle is moved according to the egress advance process in step 616-8 and the process returns to step 602 of FIG. 6A. The needle may move out of the peak stage region 502 into the egress stage region 506 while moving according to the egress advance process and movement. This movement from the peak stage region 502 to the egress stage region 506 may indicate to the user that the current stage is no longer suitable for performing the assessment related to blood flow.

Returning to step 616-2, if the absolute value of the slope has decreased, then an egress retreat counter is increased at step 616-14. If the egress retreat counter has not yet reached a first predetermined threshold (e.g., 1 second) as determined at step 616-16 and has not yet reached a second, lower, predetermined threshold (e.g., 0.5 seconds) as determined at step 616-18, then the needle is not moved and the process returns to step 602 of FIG. 6A. If the egress retreat counter has not yet reached a first predetermined threshold but has reached the predetermined threshold as determined at step 616-18, then the needle is moved according to the egress advance needle movement process of step 616-8 and the process returns to step 602 of FIG. 6A.

Figure 6F:
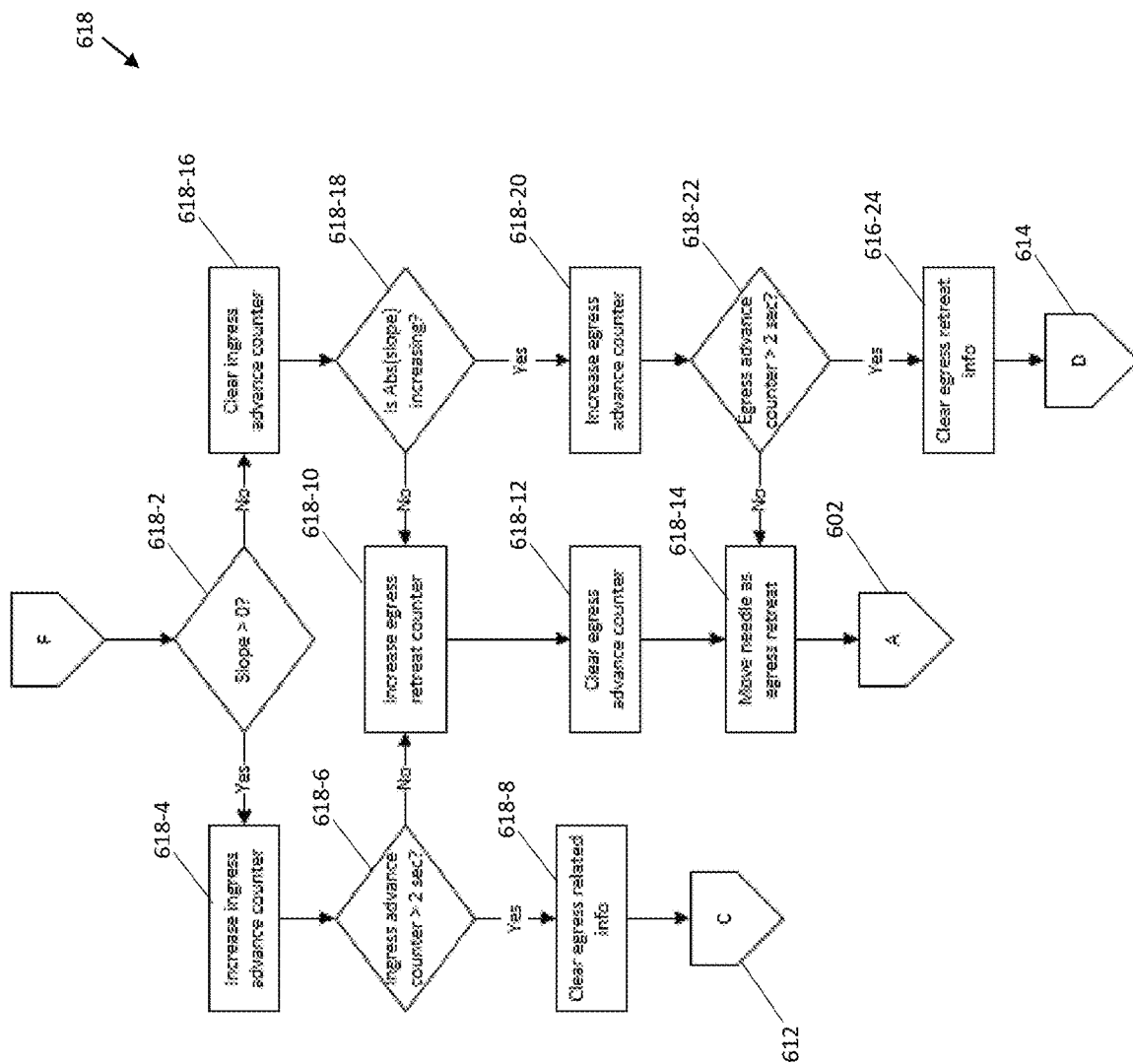

If the egress retreat counter has reached the first predetermined threshold as determined at step 616-6, the current needle location is stored as the egress retreat starting point at step 616-20 and the needle is moved according to an egress retreat process at step 618, which is shown FIG. 6F.

In FIG. 6F, at step 618-2, the check is made whether the slope is positive. If it is, then the ingress advance counter is increased at step 618-4. If the ingress advance counter is above a threshold (e.g., 2 seconds) as determined at step 618-6, then egress related information is cleared at step 618-8 and the process moves to the ingress advance step 612 of FIG. 6C. The threshold value used in the egress stages may be greater than the analogous thresholds used in the ingress stages because slope values may rise and fall more often during the egress stages than the ingress stages. If the ingress advance counter has not yet reached the threshold at step 618-6, the egress retreat counter is increased at step 618-10, the egress advance counter is cleared at step 618-12, and the needle is moved as egress retreat at step 618-14.

Similarly to the ingress retreat needle movement, the needle can be moved in the egress retreat step 618-14 according to the ratio of the current slope to the maximum slope in the egress mode, according to the following formula:

$$x = \frac{(ms - cs)}{ms} * (ns - rs)\pi$$

where
- x: target needle location (angle in radians measured counterclockwise from horizontal-right),
- ns: needle start location. (for example, with center of the slope indicator=0.5),
- cs: current slope,
- ms: max negative egress slope,
- rs: needle location when egress retreat started The needle start location is set in step 616-20 of FIG. 6E and the maximum negative egress slope is set in step 616-10 of FIG. 6E. The needle is moved to the target location in step 618-14.

Returning to step 618-2, if the slope is negative then the ingress advance counter is cleared at step 618-16 and then a check is made whether the magnitude of the slope is increasing at step 618-18. If it is not, then the process moves to step 618-10 discussed above. If the magnitude of the slope is increasing, then the egress advance counter is increased at step 618-20. If the egress advance counter has not yet met a threshold (e.g., 2 seconds) as determined at step 618-22, then the needle is moved according to the egress retreat process at step 618-14 discussed above. If the egress advance counter threshold is met, then egress retreat information is cleared at step 618-24 and the method returns to the ingress retreat process of step 614 of FIG. 6D.

Returning to step 606 of FIG. 6A, if the current status is ingress then the check at step 610 is made whether the current status is ingress advance. If it is, then the needle is moved according to the ingress advance process 612 of FIG. 6C. If the current status ingress retreat, then the needle is moved according to the ingress retreat process 614 of FIG. 6D. If the current status is egress at step 606, then a check is made at step 620 whether the current status is egress advance. If it is, then the needle is moved according to the egress advance process 616 of FIG. 6E. If the current status is egress retreat, then the needle is moved according to the egress retreat process 618 of FIG. 6F.

Figure 10B:
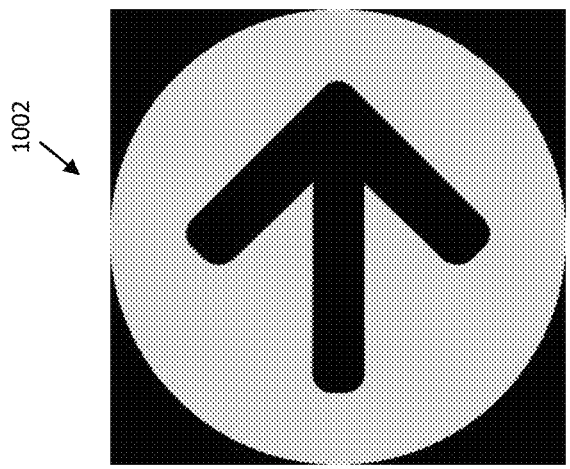
FIGS. 10A-10C illustrate additional exemplary graphical indicators that can be used for indicating the suitable stage for performing assessments related to blood flow.
Figure 10C:
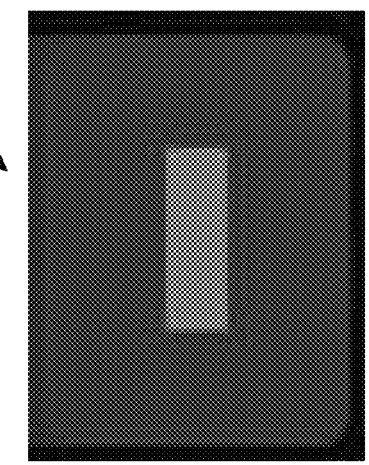
Figure 10A:
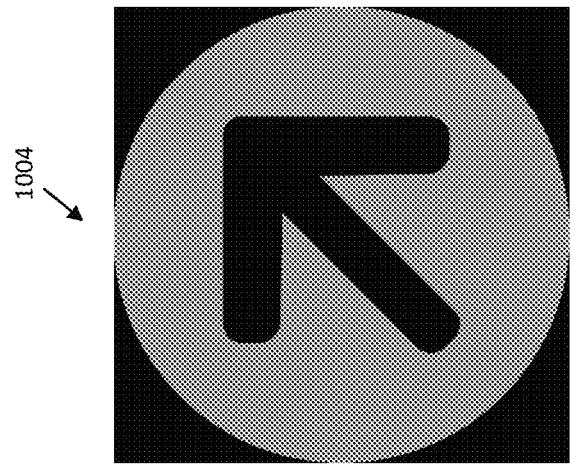

FIGS. 10A-10C illustrate additional exemplary graphical indicators 1004, 1002, and 1006 that can be used for indicating the suitable stage for performing assessments related to blood flow and/or other stages. Optionally, the ingress stage indicator 1004 may be displayed when the ingress stage is determined to be the current stage based on a fluorescence image characteristic, while the stable fluorescence stage indicator 1002 may instead be displayed when the fluorescence image characteristic indicates a stable fluorescence signal suitable for performing assessment. Optionally, there may be no indicator displayed when the ingress stage is determined to be the current stage, and the stable fluorescence stage indicator 1002 may be displayed when the fluorescence image characteristic indicates a stable fluorescence signal. Optionally, a post-stable fluorescence stage indicator 1006 or an egress stage indicator may be shown if the current stage is determined to be after the stable fluorescence stage or if the egress stage is determined to be the current stage. Alternatively, instead of displaying a post-stable fluorescence stage or an egress stage indicator if the current stage is determined to be after the stable fluorescence stage or if the egress stage is determined to be the current stage, the stable fluorescence stage indicator 1002 may cease to be displayed. Optionally, upon detecting the start of the stable fluorescence stage, a timestamp may be displayed showing the time from the onset of fluorescence until the start of the stable fluorescence stage. Optionally, the stable fluorescence stage indicator 1002 may cease to be displayed after a predefined amount of time has elapsed from detection of the onset of fluorescence, for example after about 2 minutes from the onset of fluorescence.

Optionally, a running timer may be displayed upon detection of the onset of fluorescence, with the timer displaying the time elapsed since onset. Optionally, the timer may be displayed without additional indicators. Optionally, the timer may be displayed in combination with any one or more of the other indicators as described above.

System for Accurate Blood Flow Related Assessment Timing

A system for accurate blood flow related assessment timing and timing guidance, according to some variations, can include an imaging system for acquiring at least one time series of images of tissue (e.g., a time series of fluorescence images, a time series of white light images, etc.), and one or more processors and memory having instructions stored thereon, wherein the instructions when executed by the one or more processors cause the system to perform the methods substantially as described above for determining the suitable stage of movement of a bolus of fluorescence imaging agent through imaged tissue and/or for performing one or more assessments of blood flow through the tissue based on the fluorescence images.

In some variations, the system for determining the suitable stage of movement of a bolus of fluorescence imaging agent through imaged tissue and/or for performing one or more assessments related to blood flow through the tissue based on the fluorescence images as described herein in connection with the various aspects is a fluorescence imaging system. FIG. 7 is a schematic example of a fluorescence imaging system 710. The fluorescence imaging system 710 comprises a light source 712 to illuminate the tissue of the subject to induce fluorescence emission from a fluorescence imaging agent 714 in the tissue of the subject (e.g., in blood), an image acquisition assembly 716 arranged for generating the time series and/or the subject time series of fluorescence images from the fluorescence emission, and a processor assembly 718 arranged for processing the generated time series/subject time series of fluorescence images according to any of the variations of the methods described herein. The processor assembly 718 may include memory 768 with instructions thereon, a processor module 762 arranged for executing the instructions on memory 768 to process the time series and/or subject time series of fluorescence images as described herein in connection with the various aspects of the methods, and a data storage module 764 to store the unprocessed and/or processed time series and/or subject time series of fluorescence images. In some variations, the memory 768 and data storage module 764 may be embodied in the same storage medium, while in other variations the memory 768 and the data storage module 764 may be embodied in different storage mediums. The system may further include a display 766 on which to display images and other data, such as some or all of the time series of fluorescence images or other input data, visual assessment timing guidance, visual timing stage information, results of performing an assessment based on the timing determination such as spatial maps, and/or a tissue numerical values (quantifiers) from an assessment related to blood flow.

Figure 8:
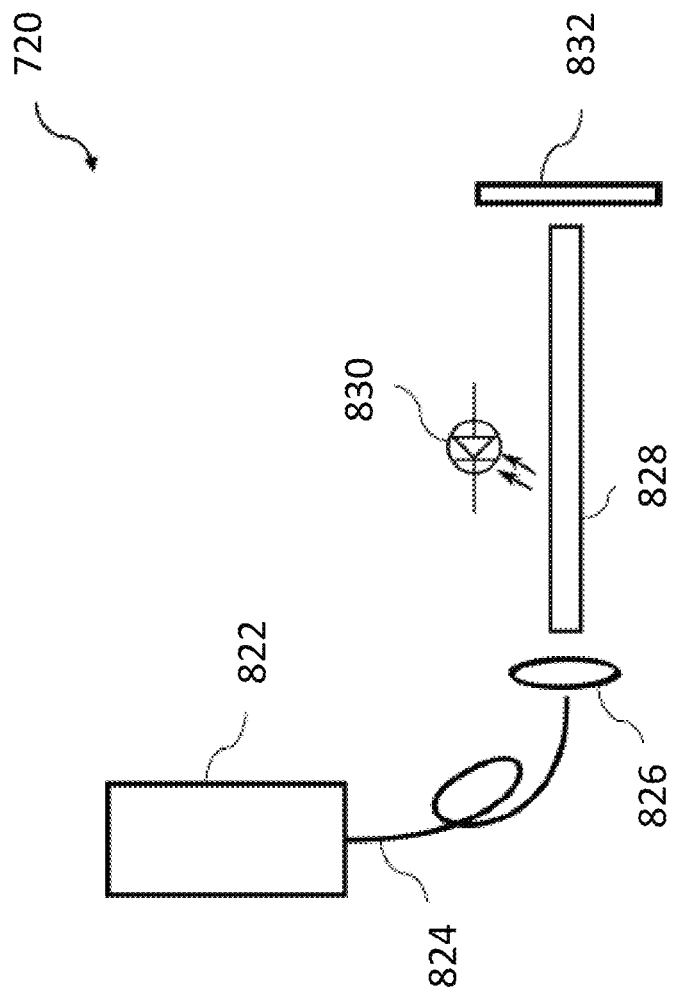
FIG. 8 is an illustrative depiction of an exemplary illumination module of a fluorescence imaging system.

In some variations, the light source 712 includes, for example, an illumination module 720. Illumination module 720 may include a fluorescence excitation source arranged for generating an excitation light having a suitable intensity and a suitable wavelength for exciting the fluorescence imaging agent 714. As shown in FIG. 8, the illumination module 720 may comprise a laser diode 822 (e.g., which may comprise, for example, one or more fiber-coupled diode lasers) arranged for providing an excitation light to excite the fluorescence imaging agent (not shown) in tissue of the subject. Examples of other sources of the excitation light which may be used include one or more LEDs, arc lamps, or other illuminant technologies of sufficient intensity and appropriate wavelength to excite the fluorescence imaging agent in the tissue. For example, excitation of the fluorescence imaging agent in blood, wherein the fluorescence imaging agent is a fluorescence dye with near infra-red excitation and emission characteristics, may be performed using one or more 793 nm, conduction-cooled, single bar, fiber-coupled laser diode modules from DILAS Diode Laser Co, Germany.

Referring again to FIG. 7, in some variations, the light output from the light source 712 may be projected through one or more optical elements to shape and guide the output being used to illuminate the tissue area of interest. The optical elements may include one or more lenses, light guides, and/or diffractive elements so as to ensure a flat field over substantially the entire field of view of the image acquisition assembly 716. The fluorescence excitation source may be selected to emit at a wavelength close to the absorption maximum of the fluorescence imaging agent 714 (e.g., ICG, etc.). For example, as shown in FIG. 8, the output 824 from the laser diode 822 may be passed through one or more focusing lenses 826, and then through a homogenizing light pipe 828 such as, for example, light pipes commonly available from Newport Corporation, USA. Finally, the light may be passed through an optical diffractive element 832 (i.e., one or more optical diffusers) such as, for example, ground glass diffractive elements also available from Newport Corporation, USA. Power to the laser diode 822 may be provided by, for example, a high-current laser driver such as those available from Lumina Power Inc. USA. The laser may optionally be operated in a pulsed mode during the image acquisition process. An optical sensor such as a solid state photodiode 830 may be incorporated into the illumination module 720 and may sample the illumination intensity produced by the illumination module 720 via scattered or diffuse reflections from the various optical elements. In some variations, additional illumination sources may be used to provide guidance when aligning and positioning the module over the area of interest.

Figure 9:
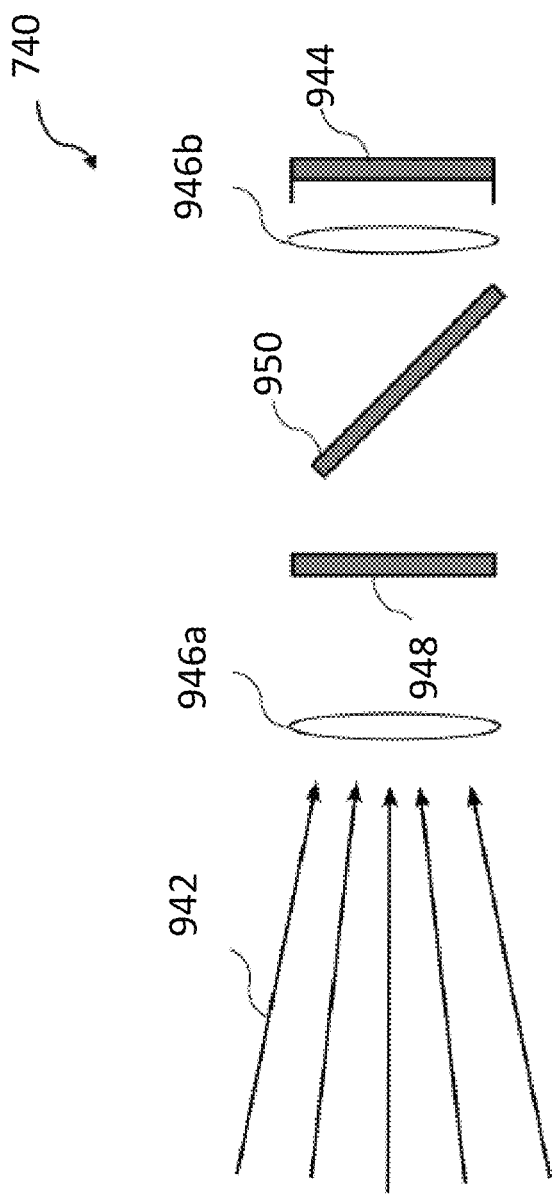
FIG. 9 is an exemplary camera module of a fluorescence imaging system.

Referring again to FIG. 7, in some variations, the image acquisition assembly 716 may be a component of a fluorescence imaging system 710 configured to acquire the time series and/or subject time series of fluorescence images from the fluorescence emission from the fluorescence imaging agent 714. The image acquisition assembly 716 can be or include an endoscopic imager, an open-field imager, a handheld imager, or any other suitable imager. The image acquisition assembly 716 may include a camera module 740. As shown in FIG. 9, the camera module 740 may acquire images of the fluorescence emission 942 from the fluorescence imaging agent in the tissue by using a system of imaging optics (e.g., 946a, 946b, 948 and 950) to collect and focus the fluorescence emission onto an image sensor assembly 944. The image sensor assembly 944 may comprise at least one 2D solid state image sensor. The solid state image sensor may be a charge coupled device (CCD), a CMOS sensor, a CID or similar 2D sensor technology. The charge that results from the optical signal transduced by the image sensor assembly 944 is converted to an electrical video signal, which includes both digital and analog video signals, by the appropriate read-out and amplification electronics in the camera module 940.

According to an exemplary variation of a fluorescent imaging system, the light source may provide an excitation wavelength of about 800 nm+/−10 nm, and the image acquisition assembly uses emission wavelengths of >820 nm with NIR-compatible optics for, for example, ICG fluorescence imaging. In an example, the NIR-compatible optics may include a CCD monochrome image sensor having a GigE standard interface and a lens that is compatible with the sensor with respect to optical format and mount format (e.g., C/CS mount).

In some variations, the processor module 762 comprises any computer or computing means such as, for example, a tablet, laptop, desktop, networked computer, or dedicated standalone microprocessor. For instance, the processor module 762 may include one or more central processing units (CPU). Optionally, the processor module 762 is a quad-core, 2.5 GHz processor with four CPUs where each CPU is a microprocessor such as a 64-bit microprocessor (e.g., marketed as INTEL Core i3, i5, or i7, or in the AMD Core FX series). However, the processor module 762 may alternatively be any suitable processor with any suitable number of CPUs and/or other suitable clock speed.

Inputs for the processor module 762 may be taken, for example, from the image sensor 944 of the camera module 740 shown in FIG. 9, from the solid state photodiode 830 in the illumination module 720 in FIG. 8, and/or from any external control hardware such as a footswitch or remote-control. Output is provided to the laser diode driver and optical alignment aids. As shown in FIG. 7, in some variations, the processor assembly 718 may have a data storage module 764 with the capability to save the time series/subject time series of images, or data representative thereof, or other input data to a tangible non-transitory computer readable medium such as, for example, internal memory (e.g. a hard disk or flash memory), so as to enable recording and processing of acquired data. In some variations, the processor module 762 may have an internal clock to enable control of the various elements and ensure correct timing of illumination and sensor shutters. In some variations, the processor module 762 may also provide user input and graphical display of outputs. The fluorescence imaging system may optionally be configured with a video display 766 or other monitor to display the time series of fluorescence images as they are being acquired or played back after recording. The video display 766 may additionally or alternatively visualize data generated during performance of the methods described herein, such as a spatial map, a subject spatial map, and/or tissue numerical value.

In operation of the exemplary system described in FIGS. 7-9, the subject is positioned relative to fluorescence imaging system 710 such that an area of interest (e.g., target tissue region) is located beneath the light source 712 and the image acquisition assembly 716 such that the illumination module 720 of light source 712 produces a substantially uniform field of illumination across substantially the entire area of interest. In some variations, prior to the administration of the fluorescence imaging agent 714 to the subject, an image may be acquired of the area of interest for the purposes of background deduction. To acquire fluorescence images/subject fluorescence images, the operator of the fluorescence imaging system 710 may initiate the acquisition of the time series of fluorescence images by depressing a remote switch or foot-control, or via a keyboard (not shown) connected to the processor assembly 718, or via a button or other user interface on a hand-held imager, such as a hand-held endoscopic imager or a hand-held open field imager. As a result, the light source 712 is turned on and the processor assembly 718 begins recording the fluorescence image data/subject fluorescence image data provided by the image acquisition assembly 716. When operating in a pulsed mode, the image sensor 944 in the camera module 740 is synchronized to collect fluorescence emission following the laser pulse produced by the diode laser 822 in the illumination module 720. In this way, maximum fluorescence emission intensity is recorded, and signal-to-noise ratio is optimized. The fluorescence imaging agent 714 can be administered to the subject and delivered to the area of interest via arterial flow. Acquisition of the time series of fluorescence images is initiated, for example, shortly after administration of the fluorescence imaging agent 714, and the time series of fluorescence images from substantially the entire area of interest is acquired throughout the ingress and egress of the fluorescence imaging agent 714. The fluorescence emission from the region of interest is collected by the collection optics of the camera module 740. Residual ambient and reflected excitation light is attenuated by subsequent optical elements (e.g., optical element 950 in FIG. 9 which may be a filter) in the camera module 740 so that the fluorescence emission can be acquired by the image sensor assembly 944 with minimal interference by light from other sources.

In some variations, following the acquisition or generation of at least a portion the time series of fluorescence images, the processor assembly 718 (e.g., processor module 762 or other processor) or one or more processors in communication with processor assembly 718 may then be initiated to execute instructions stored on memory 768 and perform one or more methods as described herein, including determining a suitable stage for performing an assessment related to blood flow in target tissue and providing guidance regarding the suitable stage to a user and/or performing the assessment automatically or in response to a user command. The system 710 may visualize on display 766 results of an assessment related to blood flow in target tissue that is performed based on the timing determination made according to the principles of any of the methods described above, including a spatial map displayed to the user as, for example, a grayscale or false color image, and/or stored for subsequent use. Additionally or alternatively, the system 710 may display on display 766 one or more tissue numerical values, including numerical values associated with one or more regions of tissue selected by a user.

In some variations, the system for tissue assessment timing and timing guidance comprises a user interface, a processor arranged for communicating with the user interface, and a non-transitory computer-readable storage medium having instructions stored which, when executed by the processor, cause the processor to perform one or more of the methods for characterizing tissue and/or predicting a clinical data described herein. In some variations, the processor may be a component of the imaging system. In other variations, the processor may be located remotely from and in communication with an imaging system, where the imaging system may be the fluorescence imaging system described above, or any suitable imaging system.

A tangible non-transitory computer readable medium having computer-executable (readable) program code embedded thereon may provide instructions for causing one or more processors to, when executing the instructions, perform one or more of the methods for tissue assessment timing and timing guidance described herein. Program code can be written in any appropriate programming language and delivered to the processor in many forms, including, for example, but not limited to information permanently stored on non-writeable storage media (e.g., read-only memory devices such as ROMs, CD-ROM disks, etc.), information alterably stored on writeable storage media (e.g., hard drives or the like), information conveyed to the processor through communication media, such as a local area network, a public network such as the Internet, or any type of media suitable for storing electronic instruction. When carrying computer readable instructions that implement the various aspects of the methods described herein, such computer readable media represent examples of various embodiments of the present invention. In various embodiments, the tangible non-transitory computer readable medium comprises all computer-readable media, and the present invention scope is limited to computer readable media wherein the media is both tangible and non-transitory.

A kit may include any part of the systems described herein and the fluorescence imaging agent such as, for example, a fluorescence dye such as ICG or any suitable fluorescence imaging agent. In further aspects, a kit may include a tangible non-transitory computer readable medium having computer-executable (readable) program code embedded thereon that may provide instructions for causing one or more processors, when executing the instructions, to perform one or more of the methods for tissue assessment timing and timing guidance described herein. The kit may include instructions for use of at least some of its components (e.g., for using the fluorescence imaging agent, for installing the computer-executable (readable) program code with instructions embedded thereon, etc.). In yet further aspects, there is provided a fluorescence imaging agent such as, for example, a fluorescence dye for use in in the methods and systems described herein. In further variations, a kit may include any part of or the entire system described herein and a fluorescence agent such as, for example, a fluorescence dye such as ICG, or any other suitable fluorescence agent, or a combination of fluorescence agents.

Exemplary Imaging Agents

Optionally, a kit may include any part of the systems described herein and a fluorescence agent such as, for example, a fluorescence dye such as ICG or any suitable fluorescence agent or a combination of fluorescence agents. In some variations, a suitable fluorescence agent is an agent which can circulate with the blood (e.g., an agent which can circulate with, for example, a component of the blood such as plasma in the blood) and which fluoresces when exposed to appropriate excitation light energy. For example, ICG, when administered to the subject, binds with blood proteins and circulates with the blood in the tissue. The fluorescence imaging agent (e.g., ICG) may be administered to the subject as a bolus injection (e.g., into a vein or an artery) in a concentration suitable for imaging such that the bolus circulates in the vasculature and traverses the microvasculature. In some variations in which multiple fluorescence imaging agents are used, such agents may be administered simultaneously, e.g. in a single bolus, or sequentially in separate boluses. Optionally, the fluorescence imaging agent may be administered by a catheter. The fluorescence imaging agent may be administered less than an hour in advance of performing the measurement of signal intensity arising from the fluorescence imaging agent. For example, the fluorescence imaging agent may be administered to the subject less than 30 minutes in advance of the measurement. The fluorescence imaging agent may be administered at least 30 seconds in advance of performing the measurement. The fluorescence imaging agent may be administered contemporaneously with performing the measurement. The fluorescence imaging agent may be administered in various concentrations to achieve a desired circulating concentration in the blood. For example, where the fluorescence imaging agent is ICG, it may be administered at a concentration of about 2.5 mg/mL to achieve a circulating concentration of about 5 µM to about 10 µM in blood. The upper concentration limit for the administration of the fluorescence imaging agent may be the concentration at which the fluorescence imaging agent becomes clinically toxic in circulating blood, and the lower concentration limit may be the instrumental limit for acquiring the signal intensity data arising from the fluorescence imaging agent circulating with blood to detect the fluorescence imaging agent. The upper concentration limit for the administration of the fluorescence imaging agent may be the concentration at which the fluorescence imaging agent becomes self-quenching. For example, the circulating concentration of ICG may range from about 2 µM to about 10 mM. Thus, in one aspect, the method comprises the step of administration of the imaging agent (e.g., a fluorescence imaging agent) to the subject and acquisition of the signal intensity data (e.g., video) prior to processing the signal intensity data according to the various embodiments. In another aspect, the method excludes any step of administering the imaging agent to the subject.

According to some aspects, a suitable fluorescence imaging agent for use in fluorescence imaging applications to generate fluorescence image data is an imaging agent which can circulate with the blood (e.g., a fluorescence dye which can circulate with, for example, a component of the blood such as lipoproteins or serum plasma in the blood) and transit vasculature of the tissue (i.e., large vessels and microvasculature), and from which a signal intensity arises when the imaging agent is exposed to appropriate light energy (e.g., excitation light energy, or absorption light energy). The fluorescence imaging agent may include a fluorescence dye, an analogue thereof, a derivative thereof, or a combination of these. An example of the fluorescence agent is a fluorescence dye, which includes any non-toxic fluorescence dye. In certain variations, the fluorescence dye may include a dye that emits light in the near-infrared spectrum. The fluorescence dye may include a tricarbocyanine dye such as, for example, indocyanine green (ICG). In other variations, the fluorescence dye may comprise methylene blue, ICG or a combination thereof. The dye may or may comprise fluorescein isothiocyanate, rhodamine, phycoerythrin, phycocyanin, allophycocyanin, o-phthaldehyde, fluorescamine, rose Bengal, trypan blue, fluoro-gold, green fluorescence protein, flavins (e.g., riboflavin, etc.), methylene blue, porphysomes, cyanine dyes (e.g., cathepsin-activated Cy5 combined with a targeting ligand, Cy5.5, etc.), IRDye800CW, CLR 1502 combined with a targeting ligand, OTL38 combined with a targeting ligand, or a combination thereof, which is excitable using excitation light wavelengths appropriate to each imaging agent. In some variations, an analogue or a derivative of the fluorescence imaging agent may be used. For example, a fluorescence dye analogue or a derivative may include a fluorescence dye that has been chemically modified, but still retains its ability to fluoresce when exposed to light energy of an appropriate wavelength. In variations in which some or all of the fluorescence is derived from autofluorescence, one or more of the fluorophores giving rise to the autofluorescence may be an endogenous tissue fluorophore (e.g., collagen, elastin, NADH, etc.), 5-aminolevulinic acid (S-ALA), or a combination thereof.

Optionally, the fluorescence imaging agent is configured to target a region of tissue and is used for visualizing the targeted region. The following is an exemplary list of imaging agents that can be used and the regions of tissue that they can target. ICG and/or Methylene blue may be used for targeting breast tissue, parathyroid tissue, and tumors. A proflavine agent can be used for targeting squamous cell neoplasia, Barrett's esophagus, colon polyps, dysplasia, anal dysplasia, head and neck cancer, cervical cancer, uterine cancer, oral disorders, and gastric cancer. ALA may be used for targeting gliomas, the bladder, and skin precancers and cancers.

Hexaminolevulinate can be used for targeting the bladder, the cervix, and colorectal cancers. Methyl aminolevulinate can be used for targeting skin actinic keratosis, cancers, Bowen's disease, and acne. A cathepsin activatable can be used for targeting sarcomas, and colorectal, pancreatic, esophageal, breast, and prostate cancers. A protease activatable can be used for targeting breast cancer. Fluorescent lectin can be used for targeting colorectal cancer, neoplasms, and polyps. An HSP90 inhibitor can be used for targeting solid tumors. A chlorotoxin blocking chloride channels with Cy5.5 can be used for targeting gliomas, other CNS tumors, breast cancer, skin cancer, and sarcomas. A 7-aa peptide-IRDye800CW can be used for targeting gastrointestinal malignancies. A c-Met targeting peptide can be used for targeting colon cancer, esophageal cancer and high grade dysplasia, papillary thyroid cancer, and lung cancer. A folate receptor targeter can be used for targeting renal cell, lung, ovarian, pituitary, and pleural cancers. Tumor-specific integrin receptor binder can be used for targeting breast cancer. Anti-EGFR binding peptide can be used for targeting colon cancer and cholangiocarcinoma. Anti-EGFR affibody can be used for targeting gliomas, sarcomas, and head and neck cancers. GRPR receptor binding peptide can be used for targeting glioblastomas. VEGF antibody can be used for targeting esophageal cancer, breast cancer, and adenomatous polyposis. EGFR antibody can be used for targeting pancreatic cancer, brain neoplasms, gliomas, head and neck squamous cell carcinoma, and head and neck cancer. Carbonic anhydrase IX antibody can be used for targeting renal cell carcinomas.

The fluorescence imaging agent may be provided as a lyophilized powder, solid, or liquid. The fluorescence imaging agent may be provided in a vial (e.g., a sterile vial), which may permit reconstitution to a suitable concentration by administering a sterile fluid with a sterile syringe. Reconstitution may be performed using any appropriate carrier or diluent. For example, the fluorescence imaging agent may be reconstituted with an aqueous diluent immediately before administration. Optionally, any diluent or carrier which will maintain the fluorescence imaging agent in solution may be used. As an example, ICG may be reconstituted with water. Optionally, once the fluorescence imaging agent is reconstituted, it may be mixed with additional diluents and carriers. Optionally, the fluorescence imaging agent may be conjugated to another molecule, such as a protein, a peptide, an amino acid, a synthetic polymer, or a sugar, for example to enhance solubility, stability, imaging properties, or a combination thereof. Additional buffering agents may optionally be added including Tris, HCl, NaOH, phosphate buffer, and/or HEPES.

A person of skill in the art will appreciate that, although fluorescence imaging agents were described above in detail, other imaging agents may be used in connection with the systems, methods, and techniques described herein, depending on the medical imaging modality.

In some variations, the fluorescence imaging agent used in combination with the methods, systems and kits described herein may be used for blood flow imaging, tissue perfusion imaging, or a combination thereof, which may be performed during an invasive surgical procedure, a minimally invasive surgical procedure, a non-invasive surgical procedure, or a combination thereof. Examples of invasive surgical procedure which may involve blood flow and tissue perfusion include a cardiac-related surgical procedure (e.g., CABG on pump or off pump) or a reconstructive surgical procedure. An example of a non-invasive or minimally invasive procedure includes wound (e.g., chronic wound such as for example pressure ulcers) treatment and/or management. In this regard, for example, a change in the wound over time, such as a change in wound dimensions (e.g., diameter, area), or a change in tissue perfusion in the wound and/or around the peri-wound, may be tracked over time with the application of the methods and systems.

In variations relating to cardiac applications or any vascular applications, the imaging agent(s) (e.g., ICG alone or in combination with another imaging agent) may be injected intravenously. For example, the imaging agent may be injected intravenously through the central venous line, bypass pump and/or cardioplegia line and/or other vasculature to flow and/or perfuse the coronary vasculature, microvasculature and/or grafts. ICG may be administered as a dilute ICG/blood/saline solution down the grafted vessel or other vasculature such that the final concentration of ICG in the coronary artery or other vasculature depending on application is approximately the same or lower as would result from injection of about 2.5 mg (i.e., 1 ml of 2.5 mg/ml) into the central line or the bypass pump. The ICG may be prepared by dissolving, for example, 25 mg of the solid in 10 ml sterile aqueous solvent, which may be provided with the ICG by the manufacturer. One milliliter of the ICG solution may be mixed with 500 ml of sterile saline (e.g., by injecting 1 ml of ICG into a 500 ml bag of saline). Thirty milliliters of the dilute ICG/saline solution may be added to 10 ml of the subject's blood, which may be obtained in an aseptic manner from the central arterial line or the bypass pump. ICG in blood binds to plasma proteins and facilitates preventing leakage out of the blood vessels. Mixing of ICG with blood may be performed using standard sterile techniques within the sterile surgical field. Ten ml of the ICG/saline/blood mixture may be administered for each graft. Rather than administering ICG by injection through the wall of the graft using a needle, ICG may be administered by means of a syringe attached to the (open) proximal end of the graft. When the graft is harvested surgeons routinely attach an adaptor to the proximal end of the graft so that they can attach a saline filled syringe, seal off the distal end of the graft and inject saline down the graft, pressurizing the graft and thus assessing the integrity of the conduit (with respect to leaks, side branches etc.) prior to performing the first anastomosis. In other variations, the methods, dosages or a combination thereof as described herein in connection with cardiac imaging may be used in any vascular and/or tissue perfusion imaging applications.

Tissue perfusion relates to the microcirculatory flow of blood per unit tissue volume in which oxygen and nutrients are provided to and waste is removed from the capillary bed of the tissue being perfused. Tissue perfusion is a phenomenon related to but also distinct from blood flow in vessels. Quantified blood flow through blood vessels may be expressed in terms that define flow (i.e., volume/time), or that define speed (i.e., distance/time). Tissue blood perfusion defines movement of blood through micro-vasculature, such as arterioles, capillaries, or venules, within a tissue volume. Quantified tissue blood perfusion may be expressed in terms of blood flow through tissue volume, namely, that of blood volume/time/tissue volume (or tissue mass). Perfusion is associated with nutritive blood vessels (e.g., micro-vessels known as capillaries) that comprise the vessels associated with exchange of metabolites between blood and tissue, rather than larger-diameter non-nutritive vessels. Optionally, quantification of a target tissue may include calculating or determining a parameter or an amount related to the target tissue, such as a rate, size volume, time, distance/time, and/or volume/time, and/or an amount of change as it relates to any one or more of the preceding parameters or amounts. However, compared to blood movement through the larger diameter blood vessels, blood movement through individual capillaries can be highly erratic, principally due to vasomotion, wherein spontaneous oscillation in blood vessel tone manifests as pulsation in erythrocyte movement.

The present disclosure encompasses a fluorescence imaging agent for use in the imaging systems and methods as described herein. Use may comprise vascular blood flow imaging, tissue perfusion imaging, or a combination thereof, which may occur during an invasive surgical procedure, a minimally invasive surgical procedure, a non-invasive surgical procedure, or a combination thereof. The fluorescence agent may be included in the kit described herein.

The invasive surgical procedure may comprise a cardiac-related surgical procedure or a reconstructive surgical procedure. The cardiac-related surgical procedure may comprise a cardiac coronary artery bypass graft (CABG) procedure which may be on pump and/or off pump.

The minimally invasive or the non-invasive surgical procedure may comprise a wound care procedure.

The methods and processes described herein may be performed by code or instructions to be executed by a computer, processor, manager, or controller, or in hardware or other circuitry.

Because the algorithms that form the basis of the methods (or operations of the computer, processor, or controller) are described in detail, the code or instructions for implementing the operations of the method embodiments may transform the computer, processor, or controller into a special-purpose processor for performing the methods described herein.

A computer-readable medium, e.g., a non-transitory computer-readable medium, may store the code or instructions described above. The computer-readable medium may be a volatile or non-volatile memory or other storage device, which may be removably or fixedly coupled to the computer, processor, or controller which is to execute the code or instructions for performing the method embodiments described herein.

The foregoing description, for the purpose of explanation, has been described with reference to specific embodiments. However, the illustrative discussions above are not intended to be exhaustive or to limit the invention to the precise forms disclosed. Many modifications and variations are possible in view of the above teachings. The embodiments were chosen and described in order to best explain the principles of the techniques and their practical applications. Others skilled in the art are thereby enabled to best utilize the techniques and various embodiments with various modifications as are suited to the particular use contemplated.

Although the disclosure and examples have been fully described with reference to the accompanying figures, it is to be noted that various changes and modifications will become apparent to those skilled in the art. Such changes and modifications are to be understood as being included within the scope of the disclosure and examples as defined by the claims. Finally, the entire disclosure of the patents and publications referred to in this application are hereby incorporated herein by reference.

The invention claimed is:

1. A method for performing an assessment related to blood flow in tissue comprising:
   receiving fluorescence imaging data associated with movement of a fluorescence imaging agent through a target;
   determining, as the fluorescence imaging data is received, at least one characteristic associated with a current stage of the movement of the fluorescence imaging agent through the target based on the fluorescence imaging data;
   comparing the at least one characteristic associated with the current stage to a threshold value corresponding to a stabilization of the movement of the fluorescence imaging agent through the target to determine whether the current stage corresponds to a suitable stage for performing an assessment related to blood flow; and
   in accordance with the current stage corresponding to the suitable stage, performing the assessment related to blood flow in at least a portion of the target based on the fluorescence imaging data.

2. The method of claim 1, wherein the suitable stage is associated with a transition from a net increase in fluorescence imaging agent to a reduced net increase, no net change, or a net decrease in fluorescence imaging agent.

3. The method of claim 1, further comprising, prior to performing the assessment related to blood flow, generating at least one indication that the current stage corresponds to the suitable stage.

4. The method of claim 1, comprising generating at least one indication of the current stage.

5. The method of claim 4, wherein the at least one indication of the current stage indicates a relative rate that a level of fluorescence imaging agent in the at least a portion of the target is increasing or decreasing.

6. The method of claim 4, wherein the at least one indication comprises a graphical indication of the current stage relative to a nominal progression associated with typical movement of fluorescent imaging agent through tissue.

7. The method of claim 3, wherein generating the at least one indication is performed in response to a user input.

8. The method of claim 3, wherein the at least one indication comprises a graphical indication.

9. The method of claim 8, wherein the graphical indication indicates a relative leveling over time of an amount of fluorescence imaging agent in the at least a portion of the target.

10. The method of claim 3, wherein the at least one indication comprises an audible indication.

11. The method of claim 3, wherein the blood flow is assessed in response to a user input received after the at least one indication is generated.

12. The method of claim 1, wherein the blood flow is assessed automatically in response to determining that the current stage corresponds to the suitable stage.

13. The method of claim 1, wherein performing the assessment related to blood flow comprises assessing tissue perfusion of the at least a portion of the target.

14. The method of claim 1, wherein performing the assessment related to blood flow comprises quantifying tissue perfusion.

15. The method of claim 1, wherein the at least one characteristic comprises a rate of change of a level of fluorescence intensity.

16. The method of claim 15, wherein the level of fluorescence intensity is an average fluorescence intensity.

17. The method of claim 1, wherein the at least one characteristic comprises a standard deviation of fluorescence intensity.

18. The method of claim 1, wherein comparing the at least one characteristic to the threshold value comprises comparing a current rate of change of a level of fluorescence intensity to a previous rate of change of the level of fluorescence intensity.

19. The method of claim 1, wherein the fluorescence imaging data is received from an imager during a medical procedure.

20. The method of claim 1, wherein the fluorescence imaging data comprises endoscopic imaging data or open-field imaging data.

21. A system for guiding assessment related to blood flow comprising:
   one or more processors;
   memory; and
   one or more programs, wherein the one or more programs are stored in the memory and configured to be executed by the one or more processors, the one or more programs including instructions for:
   receiving fluorescence imaging data associated with a fluorescence imaging agent moving through a target;
   determining, as the fluorescence imaging data is received, at least one characteristic associated with a current stage of movement of the fluorescence imaging agent through the target based on the fluorescence imaging data;
   comparing the at least one characteristic associated with the current stage to a threshold value corresponding to a stabilization of the movement of the fluorescence imaging agent through the target to determine whether the current stage corresponds to a suitable stage for performing an assessment related to blood flow; and
   in accordance with the current stage corresponding to the suitable stage, performing the assessment related to blood flow in at least a portion of the target based on the fluorescence imaging data.

22. The system of claim 21, further comprising an imager for generating the fluorescence imaging data associated with a fluorescence imaging agent moving through a target.

23. The system of claim 21, further comprising an illuminator for generating excitation light for exciting the fluorescence imaging agent.

24. A non-transitory computer readable storage medium storing one or more programs for execution by one or more processors of a system for guiding assessment related to blood flow, the one or more programs comprising instructions for:

receiving fluorescence imaging data associated with a fluorescence imaging agent moving through a target;

determining, as the fluorescence imaging data is received, at least one characteristic associated with a current stage of movement of the fluorescence imaging agent through the target based on the fluorescence imaging data;

comparing the at least one characteristic associated with the current stage to a threshold value corresponding to a stabilization of the movement of the fluorescence imaging agent through the target to determine whether the current stage corresponds to a suitable stage for performing an assessment related to blood flow; and in accordance with the current stage corresponding to the suitable stage, performing the assessment related to blood flow in at least a portion of the target based on the fluorescence imaging data.

\* \* \* \* \*